(12) United States Patent
Tsai

(10) Patent No.: US 9,121,008 B2
(45) Date of Patent: Sep. 1, 2015

(54) DEVELOPMENT OF NATURAL KILLER CELLS AND FUNCTIONAL NATURAL KILLER CELL LINES

(75) Inventor: Schickwann Tsai, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 865 days.

(21) Appl. No.: 11/216,837

(22) Filed: Aug. 31, 2005

(65) Prior Publication Data
US 2007/0048290 A1 Mar. 1, 2007

(51) Int. Cl.
*C12N 5/0783* (2010.01)
*C12N 5/0789* (2010.01)

(52) U.S. Cl.
CPC .......... *C12N 5/0646* (2013.01); *C12N 2501/23* (2013.01); *C12N 2501/26* (2013.01); *C12N 2501/42* (2013.01); *C12N 2502/1394* (2013.01); *C12N 2502/99* (2013.01)

(58) Field of Classification Search
None
See application file for complete search history.

(56) References Cited

U.S. PATENT DOCUMENTS

| 6,849,452 | B1 | 2/2005 | Zitvogel et al. | 435/347 |
|---|---|---|---|---|
| 2002/0001826 | A1 | 1/2002 | Wager et al. | 435/325 |
| 2003/0068306 | A1 | 4/2003 | Dilber | 435/372 |
| 2003/0084471 | A1 | 5/2003 | Beach et al. | 800/13 |
| 2004/0171148 | A1 | 9/2004 | Schmitt et al. | |

FOREIGN PATENT DOCUMENTS

| CA | 2519535 | 9/2005 |
|---|---|---|
| EP | 1 452 594 A1 | 9/2004 |
| WO | WO 98/49268 | 11/1998 |
| WO | WO 2005/047300 | 5/2005 |
| WO | WO 2005/059102 | 6/2005 |

OTHER PUBLICATIONS

DeHart et al (Blood 2005, 105(6): 3521-3527, prepublished online Jan. 13, 2005).*
Luo et al (Mol. Cell. Biol. 1997, 17(10): 6057-6067).*
Fahey et al. (Clinical Experimental Immunology, 1992, 88: 1-5).*
Letvin, (Science, 1998, 280: 1875-1880).*
Machuca et al.(Intervirology 1999, 42: 37-42).*
Iannello et al (J. Leukocyte Biol. 2008, 81: 27-49).*
Artavanis-Tsakonas S, et al. (1999) Notch signaling: cell fate control and signal integration in development. Science. 284(5415):770-776.
Bettenhausen B, et al. (1995) Transient and restricted expression during mouse embryogenesis of Dll1, a murine gene closely related to Drosophila delta. Development. 121(8):2407-2418.
Bradley A, et al. (1986) Embryo-derived stem cells: a tool for elucidating the developmental genetics of the mouse. Curr Top Dev Biol. 20:357-371.

Carlyle Jr, et al. (1997) Identification of a novel developmental stage marking lineage commitment of progenitor thymocytes. J Exp Med. 186(2):173-182.
del Amo FF, et al. (1993) Cloning, analysis, and chromosomal localization of Notch-1, a mouse homolog of Drosophila Notch. Genomics. 15(2):259-264.
Dunwoodie SL, et al. (1997) Mouse D113: a novel divergent Delta gene which may complement the function of other Delta homologues during early pattern formation in the mouse embryo. Development. 124(16):3065-3076.
Elbashir SM, et al. (2001) RNA interference is mediated by 21- and 22-nucleotide RNAs. Genes Dev. 15(2):188-200.
Felli MP, et al. (1999) Expression pattern of notch1, 2 and 3 and Jagged1 and 2 in lymphoid and stromal thymus components: distinct ligand-receptor interactions in intrathymic T cell development. Int Immunol. 11(7):1017-1025.
Gammaitoni L, et al. (2004) Elevated telomerase activity and minimal telomere loss in cord blood long-term cultures with extensive stem cell replication. Blood. 103(12):4440-4448.
Hill DP, et al. (1993) Screening for novel pattern formation genes using gene trap approaches. Methods Enzymol. 225:664-681.
Hozumi K, et al. (2003) Active form of Notch members can enforce T lymphopoiesis on lymphoid progenitors in the monolayer culture specific for B cell development. J Immunol. 170(10):4973-4979.
Hozumi K, et al. (2004) Delta-like 1 is necessary for the generation of marginal zone B cells but not T cells in vivo. Nat Immunol. 5(6):638-644.
Hozumi K, et al. (2005) Active form of Notch members can enforce T lymphopoiesis on lymphoid progenitors in the monolayer culture specific for B cell development. Blood. 105(11):4290-4297.
Hutvágner G, et al. (2002) RNAi: nature abhors a double-strand. Curr Opin Genet Dev. 12(2):225-232.
Ikawa T, et al. (1999) Commitment of common T/Natural killer (NK) progenitors to unipotent T and NK progenitors in the murine fetal thymus revealed by a single progenitor assay. J Exp Med. 190(11):1617-1626.
Itoh K, et al. (1989) Reproducible establishment of hemopoietic supportive stromal cell lines from murine bone marrow. Exp Hematol. 17(2):145-153.
Jaleco AC, et al. (2001) Differential effects of Notch ligands Delta-1 and Jagged-1 in human lymphoid differentiation. J Exp Med. 194(7):991-1002.
Jiang R, et al. (1998) Defects in limb, craniofacial, and thymic development in Jagged2 mutant mice. Genes Dev. 12(7):1046-1057.
Karlhofer FM, et al. (1995) Ly-49-independent natural killer (NK) cell specificity revealed by NK cell clones derived from p53-deficient mice. J Exp Med. 181(5):1785-1795.
Kato K, et al. (2000) ESOP-1, a secreted protein expressed in the hematopoietic, nervous, and reproductive systems of embryonic and adult mice. Blood. 96(1):362-364.
Katsura Y. (2002) Redefinition of lymphoid progenitors. Nat Rev Immunol. 2(2):127-132.
Kim S, et al. (2002) In vivo developmental stages in murine natural killer cell maturation. Nat Immunol. 3(6):523-528.

(Continued)

*Primary Examiner* — Gerald R Ewoldt
*Assistant Examiner* — Marianne Dibrino
(74) *Attorney, Agent, or Firm* — Ballard Spahr LLP

(57) ABSTRACT

The invention relates to natural killer cells and methods for the development of immortalized natural killer cells and use of the natural killer cells. A growth and culture system is described that supports increased natural killer cell development, and provides for the establishment of continuous natural killer cell lines. Additionally, the disclosed method for generating natural killer cells may be used to produce large numbers of natural killer cells for therapeutic applications and for natural killer cell research.

21 Claims, 7 Drawing Sheets

(56) References Cited

OTHER PUBLICATIONS

King AG, et al. (2002) Lineage infidelity in myeloid cells with TCR gene rearrangement: a latent developmental potential of proT cells revealed by ectopic cytokine receptor signaling. Proc Natl Acad Sci U S A. 99(7):4508-4513.

Kodama H, et al. (1994) Involvement of the c-kit receptor in the adhesion of hematopoietic stem cells to stromal cells. Exp Hematol. 22(10):979-984.

Kondo M, et al. (1997) Identification of clonogenic common lymphoid progenitors in mouse bone marrow. Cell. 91(5):661-72.

Konstantinidis KV, et al. (2005) Targeting IL-2 to the endoplasmic reticulum confines autocrine growth stimulation to NK-92 cells. Exp Hematol. 33(2):159-164.

Kubota A, et al. (1999) Diversity of NK cell receptor repertoire in adult and neonatal mice. J Immunol. 163(1):212-216.

Kuppen PJ, et al. (1994) Soluble factors produced by macrophages/monocytes inhibit lymphokine-activated killer activity in rat splenocyte cultures. Cancer Immunol Immunother. 38(1):61-67.

Kuppen PJ, et al. (1994) The infiltration of experimentally induced lung metastases of colon carcinoma CC531 by adoptively transferred interleukin-2-activated natural killer cells in Wag rats. Int J Cancer. 56(4):574-579.

Lardelli M, et al. (1994) The novel Notch homologue mouse Notch 3 lacks specific epidermal growth factor-repeats and is expressed in proliferating neuroepithelium. Mech Dev. 46(2):123-136.

Lewis J. (1998) Notch signalling and the control of cell fate choices in vertebrates. Semin Cell Dev Biol. 9(6):583-589.

Lindsell CE, et al. (1995) Jagged: a mammalian ligand that activates Notch1. Cell. 80(6):909-917.

Lister J, et al. (1995) Autologous peripheral blood stem cell transplantation and adoptive immunotherapy with activated natural killer cells in the immediate posttransplant period. Clin Cancer Res. 1(6):607-614.

Luo B, et al. (1997) Isolation and functional analysis of a cDNA for human Jagged2, a gene encoding a ligand for the Notch1 receptor. Mol Cell Biol. 17(10):6057-6067.

Nakano T, et al. (1994) Generation of lymphohematopoietic cells from embryonic stem cells in culture. Science. 265(5175):1098-1101.

Paling NR. (2003) Tyrosine phosphatase SHP-1 acts at different stages of development to regulate hematopoiesis. J Immunol. 170(10):4973-4979.

Pui JC, et al. (1999) Notch1 expression in early lymphopoiesis influences B versus T lineage determination. Immunity. 11(3):299-308.

Radtke F, et al. (1999) Deficient T cell fate specification in mice with an induced inactivation of Notch1. Immunity. 10(5):547-558.

Radtke F, et al. (2004) Notch regulation of lymphocyte development and function. Nat Immunol. 5(3):247-253.

Rosenberg SA, et al. (1987) A progress report on the treatment of 157 patients with advanced cancer using lymphokine-activated killer cells and interleukin-2 or high-dose interleukin-2 alone. N Engl J Med. 316(15):889-897.

Schmitt TM, et al. (2002) Induction of T cell development from hematopoietic progenitor cells by delta-like-1 in vitro. Immunity. 17(6):749-756.

Schmitt TM, et al. (2004) Induction of T cell development and establishment of T cell competence from embryonic stem cells differentiated in vitro. Nat Immunol. 5(4):410-417.

Schmitt TM, et al. (2004) Maintenance of T cell specification and differentiation requires recurrent notch receptor-ligand interactions. J Exp Med. 200(4):469-479.

Shawber C, et al. (1996) Jagged2: a serrate-like gene expressed during rat embryogenesis. Dev Biol. 180(1):370-376.

Shuey DJ, et al. (2002) RNAi: gene-silencing in therapeutic intervention. Drug Discov Today. 7(20):1040-1046.

Shutter JR, et al. (2000) Dll4, a novel Notch ligand expressed in arterial endothelium. Genes Dev. 14(11):1313-1318.

Simpson P. (1995) Developmental genetics. The Notch connection. Nature. 375(6534):736-737.

Spangrude GJ, et al. (1995) Long-term repopulation of irradiated mice with limiting numbers of purified hematopoietic stem cells: in vivo expansion of stem cell phenotype but not function. Blood. 85(4):1006-1016.

Spits H, et al. (1998) Early stages in the development of human T, natural killer and thymic dendritic cells. Immunol Rev. 165:75-86.

Tanigaki K, et al. (2002) Notch-RBP-J signaling is involved in cell fate determination of marginal zone B cells. Nat Immunol. 3(5):443-450.

Tax FE, et al. (1994) Sequence of *C. elegans* lag-2 reveals a cell-signalling domain shared with Delta and Serrate of *Drosophila*. Nature. 368(6467):150-154.

Tsai S, et al. (1993) A dominant negative retinoic acid receptor blocks neutrophil differentiation at the promyelocyte stage. Proc Natl Acad Sci U S A. 90(15):7153-7157.

Tsai S, et al. (1994) Lymphohematopoietic progenitors immortalized by a retroviral vector harboring a dominant-negative retinoic acid receptor can recapitulate lymphoid, myeloid, and erythroid development. Genes Dev. 8(23):2831-2841.

Tsai S, et al. (2000) T Mouse Jagged2 is differentially expressed in hematopoietic progenitors and endothelial cells and promotes the survival and proliferation of hematopoietic progenitors by direct cell-to-cell contact. Blood. 96(3):950-957.

Uyttendaele H, et al. (1996) Notch4/int-3, a mammary proto-oncogene, is an endothelial cell-specific mammalian Notch gene. Development. 122(7):2251-2259.

Weinmaster G, et al. (1992) Notch2: a second mammalian Notch gene. Development. 116(4):931-941.

Wold F. (1981) In vivo chemical modification of proteins (post-translational modification). Annu Rev Biochem. 50:783-814.

Yokoyama WM, et al. (2004) The dynamic life of natural killer cells. Annu Rev Immunol. 22:405-429.

Zamore PD, et al. (2000) RNAi: double-stranded RNA directs the ATP-dependent cleavage of mRNA at 21 to 23 nucleotide intervals. 101(1):25-33.

Official Action issued Jun. 20, 2012 for Canadian Patent Application No. 2,519,535 filed Sep. 14, 2005 (Univ. of Utah Res. Foundation—Applicant // S. Tsai—Inventor) (3 pages).

* cited by examiner

DEVELOPMENT OF NATURAL KILLER CELLS AND FUNCTIONAL NATURAL KILLER CELL LINES

TECHNICAL FIELD

This invention relates generally to biotechnology, more particularly, to natural killer cells and methods for the development of natural killer cells and use of natural killer cells.

BACKGROUND OF THE INVENTION

Natural killer (NK) cells are cytolytic lymphocytes, distinct from B-lymphocytes and T-lymphocytes, that participate in both innate immunity and adaptive immunity. NK cells lack B-cell receptors and T-cell receptors. NK cells play a key role in the elimination of tumor cells or negative major histocompatibility complex (MHC) class I cell variants. NK cells generally kill cells by releasing pore-forming proteins called perforins, proteolytic enzymes called granzymes, and chemokines. NK cells appear to use a dual receptor system in determining whether to kill or not kill potential target cells. Hence, NK cells play an important role in nonspecific antitumor immunity and prevent the establishment of primitive or metastatic tumors in both immunocompetent and immunosuppressed hosts. In particular, the role of NK cells in anti-tumor immunosurveillance has been suggested in mice (see, U.S. Pat. No. 6,849,452).

Because of their non-specific cytotoxic properties for antigen and their efficacy, NK cells constitute an important population of cells for the development of immunoadoptive approaches to the treatment of cancer or infectious diseases. Anti-tumor adoptive immunotherapy approaches have been described in the literature. Thus, in certain situations, for example, patients with malign lymphomas, the results of administering adherent NK cells with small doses of interleukin-2 (IL-2) have been promising in an adjuvant situation. NK cells have also been used for experimental treatment of different types of tumors and certain clinical studies have been initiated (Kuppen et al., 1994; Lister et al., 1995; Rosenberg et al., 1987).

Further, such cells can also be used in vitro and in vivo for lysis of cells which do not express MHC class I molecules, and more generally any cell that is sensitive to NK cells.

Adaptable therapies using NK cells (for example, treatment of human tumors or infectious diseases) or any other in vitro or in vivo use of NK cells frequently involves ex vivo expansion and activation of the NK cells.

Notch receptors and DSL (Delta-Serrate-Lag2) ligands assist in cell fate decisions during embryogenesis (Simpson et al., 1995; Robey et al., 1997; Lewis et al., 1998; Artavanis-Tsakonas et al., 1999; and Tax et al., 1994). Four Notch receptors (Notch-1, -2, -3 and -4) (del Amo et al., 1993; Weinmaster et al., 1992; Lardelli et al., 1994; and Uyttendaele et al., 1996) and five DSL ligands (Jagged1, Jagged2, Delta-like-1 or Dll-1, Dll-3 and Dll-4) (Lindsell et al., 1995; Shawber et al., 1996; Tsai et al., 2000; Bettenhausen et al., 1995; Dunwoodie et al., 1997; and Shutter et al., 2000) have been identified in the murine system. After birth, mice continue to express Notch receptors and DSL ligands in many tissues. However, little is known about their functions in adult mice. Recently, reverse genetics and cell culture studies have begun to shed light on the functional roles of Notch receptors and DSL ligands in T and B cell development (Pui et al., 1999; Radtke et al., 1999; Tanigaki et al., 2002; Radtke et al., 2004; Schmitt et al., 2002; and Schmitt et al., 2004). Conditional knockout of Notch-1 in the postnatal period abolishes T cell development (Radtke et al., 1999). The thymuses of these knockout mice also lack a well-developed cortex.

In tissue culture, Lin$^-$ Sca-1$^+$ c-Kit$^+$ murine hematopoietic stem cells (HSC) stimulated by Flt3 ligand (Flt3L), interleukin-7 (IL-7) and OP-9 stromal fibroblasts expressing ectopic Dll-1 undergo de novo T cell development (Schmitt et al., 2002) (see also, U.S. Patent Application No. 2004/0171148). Similar findings were made using progenitors derived from embryonic stem cells (ESC) (Schmitt et al., 2004). Subsequent studies indicate that continued presence of Dll-1 is required for T cell commitment and maintenance at the double-negative 1 (DN1) and 2 (DN2) stages of thymocyte development. In its absence, the developing DN1 and DN2 thymocytes adopt the NK cell fate by default (Schmitt et al., 2004). More recently, it was reported that a conditional knockout of Dll-1 blocks the development of marginal B cells, but has no effect on T cell development (Hozumi et al., 2004). This observation seems to contradict the findings of the Dll-1 studies (Schmitt et al., 2002; Schmitt et al., 2004). Nonetheless, the results of these studies underscore the importance of DSL ligands in lymphopoiesis.

BRIEF SUMMARY OF THE INVENTION

The invention relates to natural killer cells, methods for the development of natural killer cells, natural killer cell lines, and use of the natural killer cells and cell lines of the invention.

BRIEF DESCRIPTION OF THE SEVERAL VIEWS OF THE DRAWINGS

FIG. 1A shows retroviral vector-mediated expression of the full-length mJagged2 in OP-9S/LMJSN, but not OP-9S/LXSN (negative control). The top panel is a Northern blot hybridized with a mJagged2 cDNA probe. The middle panel is the ethidium bromide-stained gel before blotting. The bottom panel is a Western blot probed with rabbit anti-serum against the intracellular domain of mJagged2. The 120-kDa mJagged2 protein is indicated. FIG. 1B shows expression of NK1.1 vs. CD3 and CD19 vs. B220 by 5-FU bone marrow MNC co-cultured with OP-9S/LXSN (negative control) or OP-9S/LMJSN ("J2") in the presence of IL-7 and Flt3L for 19 days without or with IL-2 on days 10-19. The percentage of CD3– NK1.1$^+$ cells is indicated. FIG. 1C shows expression of NK1.1 vs. CD3 and CD19 vs. B220 by post-5-FU bone marrow MNC co-cultured with OP-9S/LXSN or OP-9S/LMJSN ("J2") in the presence of IL-7 and Flt3L for 28 days without or with IL-2 on days 20-28. The percentage of CD3$^-$ NK1.1$^+$ cells is indicated. Small numbers of CD3$^+$ NK1.1$^+$ cells were present in OP-9S/LMJSN co-cultures. They likely represented pT/NK or cytotoxic lymphocytes that had evolved from pre-existing T cells.

FIG. 3A shows phase-contrast microscopy of KIL at 37° C. Most KIL cells display the characteristic racket shape. Bar=30 µm. FIG. 3B shows the survival of KIL in response to single cytokines. KIL cells were washed with phosphate buffered saline and exposed to various cytokines at the indicated concentrations. Viable cells were counted after 4 days and expressed as percentage of the maximal response. Each point represents the mean of triplicates. FIG. 3C shows that stem cell factor (SCF) synergized with IL-7 to stimulate the proliferation of KIL. Each culture was started with 5×10$^5$ washed KIL cells. Cell numbers were determined on days 2, 4 and 6. Each point represents the mean of triplicates.

FIG. 4A illustrates flow cytometric analysis of the expression of Ly5.1 (CD45), CD3, NK1.1, CD25, CD4, CD8, CD19 and Mac-1. Thin line: isotype control. FIG. 4B shows nested PCR analyses of D-J rearrangements of TCRβ loci. Genomic DNAs of W20 stromal fibroblasts (negative control) (Tsai et al., 2000), B6D2F1 spleen cells (positive control) and KIL were first amplified using external primer sets (Dβ1.1ext/Jβ1.7ext or Dβ2.1ext/Jβ2.7ext) and then re-amplified using internal primer sets (Dβ1.1int/Jβ1.7int or Dβ2.1int/Jβ2.7int). Aliquots of secondary PCR reactions were run on agarose gels and stained with ethidium bromide. DNA fragments resulting from amplification of the germ-line loci are indicated. FIG. 4C shows the same blots in FIG. 4B, which were probed with $^{32}$P-labeled Dβ1.1-Jβ1.7 or Dβ2.1-Jβ2.7 probes. All DNAs amplified from the germ-line and rearranged D-J loci hybridize specifically to the respective probe.

FIG. 6A illustrates the growth curve of KIL stimulated with human IL-2 (20 ng/mL) alone. The vertical axis is plotted on a logarithmic scale. Each point represents the mean of triplicates. FIG. 6B shows Wright-Giemsa-stained KIL cells. Note the fine azurophilic granules in the cytoplasm. Bar=20 μm. FIG. 6C Wright-Giemsa-stained KIL stimulated with IL-2 (20 ng/mL) alone for 6 days. Note the larger cell size, ruffled cell membrane and prominent azurophilic granules. Bar=20 μm. FIG. 6D is a Western analysis of the expression of granzyme B by KIL stimulated with IL-2 alone for 0, 3, 6, 9 and 11 days. The 32-kDa granzyme B is indicated. Low-level granzyme B expression was detectable in the day 0 sample on the original film. The same blot was re-probed with an anti-β-actin antibody. FIG. 6E shows Northern and Western analyses of Notch-1 expression in KIL stimulated with IL-2 alone for 0 and 6 days and in the promyelocyte cell line, MPRO (negative control) (Tsai et al., 1993). The Northern blot (upper panel) was hybridized to a cDNA probe encoding the intracellular domain of mNotch1. The ethidium bromide-stained gel is shown in the middle panel. The bottom panel is a Western blot probed with affinity-purified antibodies against the carboxy terminus of mNotch1. The 120-kDa fragment of mNotch1 is indicated. FIG. 6F illustrates cytolytic activity of KIL. KIL cells were incubated with monolayers of OP-9S at 1:1 to 4:1 effector-to-target ratios in a 12-well plate in growth medium containing IL-7 and SCF. KIL lysed the OP-9S monolayers in 24-48 hours. The OP-9S monolayers were then fixed and stained with Coomassie blue. Lysed or denuded areas (†) of the OP-9S monolayers appear clear while the intact areas (*) appear blue. FIG. 6G shows the relationship between the degree of cell lysis and the effector-to-target ratio.

DETAILED DESCRIPTION OF THE INVENTION

Figure 1:
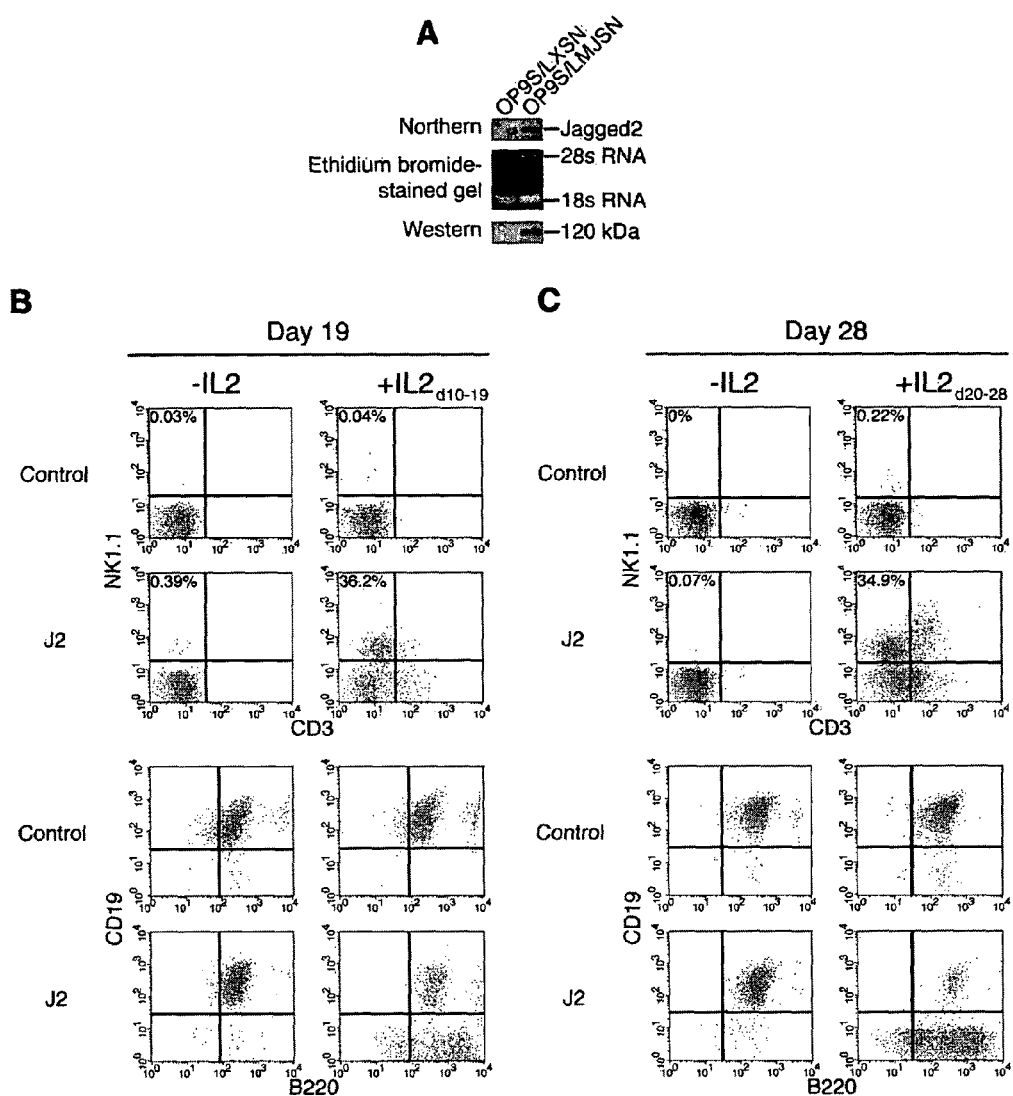
FIGS. 1A to 1C show that Jagged2 stimulates the development of NK cells from post-5-FU bone marrow MNC.

As used herein, "peptide," "polypeptide" and "protein" include polymers of two or more amino acids of any length. No distinction, based on length, is intended between a peptide, a polypeptide or a protein.

As used herein, "NK cells" means cytotoxic effector cells with the capacity to lyse tissue culture cells without participation of an antibody and without in vitro or in vivo sensitization. NK cells may also be characterized by the presence of cell surface receptors or proteins that distinguish NK cells from other lymphoid cells, and cells of the erythroid or myeloid lineages, for example, see, Bradshaw et al., Handbook of Cell Signaling (2003).

As used herein Jagged2" means a member of the Jagged2 family, including, but not limited to, mouse Jagged2 (mJagged2), rat Jagged2 (rJagged2), human Jagged2 (hJagged2), homologues, orthologues and/or paralogues of mJagged2 or hJagged2, and/or a fragment thereof, wherein the fragment is capable of binding to a Notch receptor polypeptide present in mammalian cells, such as hematopoietic stem cells, and increasing the production of NK cells. "Jagged2" also includes a mutant or variant of a known Jagged2 that is capable of increasing the production of NK cells. The Notch receptors that have been identified in human cells include Notch-1, Notch-2, Notch-3, and Notch-4.

As used herein, "hematopoietic stem cell" (HSC) refers to a cell and/or cell preparation that supports induction of a precursor NK cell line or NK cell line and encompasses "hematopoietic cells", "hematopoietic stem cells", "embryonic stem cells", "hematopoietic cell preparation", "hematopoietic progenitor cells", "Lin$^-$ Sca-1$^+$ c-Kit$^+$ cells", "Lin$^-$ Sca-1$^+$ c-Kit$^+$ HSC", "HSC", "Post-5-FU bone marrow MNC", and "CD3$^-$ NK1.1$^-$ post-5-FU bone marrow MNC".

HSCs and/or stem cells are capable of prolonged propagation and capable of further differentiation to more mature cell types (e.g., NK cells). Hematopoietic stem cells that are Lin$^-$ Sca-1$^+$ and c-kit$^+$ are preferably used in the methods and systems of the invention.

As used herein, "cells capable of differentiation into NK cells" refers to HSCs that differentiate into NK cells, when Jagged2, Flt3L, IL-7, and SCF are expressed in co-cultured cells or added to the growth media. Optionally, IL-2 may be supplied. Cells capable of differentiation into NK cells may be genetically modified either in vivo or in vitro, for example, reporter constructs may be introduced, or therapeutic gene products may by introduced or alternatively regulated.

As used herein, "suitable cell preparations" include, but are not limited to, stromal cell lines expressing a Notch receptor ligand of the Delta family. Examples of stromal cell lines that can be engineered to express a Notch receptor ligand of the Delta family are the mouse stromal cell lines OP-9 (Nakano et. al., 1994), OP-9S, MS5 (Itoh et. al., 1989) and S17, and the human stromal cell lines HGS2.11, HGS2.52, HGS.18, HGS3.30, HGS3.65, HGS3.66 HGS3.103, and HGS3.114 available from Human Genome Sciences Inc. (MD) (see U.S. App. 2002/0001826).

In accordance with the present invention, conventional molecular biology, microbiology, and recombinant DNA techniques known to a person of ordinary skill in the art may be used. See, for example, Sambrook et al., Molecular Cloning, $2^{nd}$ ed. (1989); Glover et al., DNA Cloning: A Practical Approach, Volumes I and II (1985); Gait et al., Oligonucleotide Synthesis: A Practical Approach (1984); Hames et al., Nucleic Acid Hybridization: A Practical Approach (1985); Hames et al., Transcription and Translation: A Practical Approach (1984); Freshney, Animal Cell Culture: A Manual of Basic Techniques, $3^{rd}$ ed. (1994); Guilbault et al., Immobilized Cells and Enzymes: A Practical Approach (1984); and Perbal, et al., A Practical Guide to Molecular Cloning (1988).

Cells of the invention can be grown and cultured using methods well known in the art, for example, Robertson, et. al., Teratocarcinomas and Embryonic Stem Cells: A Practical Approach (1987); Bradley et al., 1986; and Hogan et al., Manipulating the Mouse Embryo: A Laboratory Manual (1986).

Materials and Methods

Stromal Cell Lines and Retroviral Infection.

A slow-growing derivative of the original OP-9 cell line (Kodama et al., 1994), designated as OP-9S, was established and maintained in Dulbecco's Modified Eagle's medium (DME; Gibco, Grand Island, N.Y.)/30% fetal bovine serum (FBS). The original OP-9 was obtained from the laboratory of H. Kodama (Ohu University, Koriyama, Fukushima, Japan). OP-9S has a doubling time of 48-72 hours. This OP-9S cell line is deposited under the Budapest Treaty on the International Procedure at the American Type Culture Collection, 10801 University Boulevard, Manassas, Va. 20110-2209 given the accession number PTA-10785. The deposit was made on Apr. 7, 2010. W20 is a stromal fibroblast cell line derived from the bone marrow of a $W^{+/+}$ mouse (Tsai et al., 2000). It was maintained in DME/10% FBS. The construction of the retroviral vectors LXSN and LMJSN (expressing full-length mJagged2; GenBank accession no. AF038572) and the establishment of the corresponding retroviral producer cell lines have been described previously (Tsai et al., 2000). OP-9S was infected with retroviral vectors LXSN and LMJSN and selected with G418 (0.75 mg/mL) for 12 days. The resultant cell lines are designated as OP-9S/LXSN and OP-9S/LMJSN, respectively.

Post-5-fluorouracil Bone Marrow and Purification of Lin$^-$ Sca-1$^+$ c-Kit$^+$ HSC.

For post-5-fluorouracil (post-5-FU) bone marrow, 4-6-week-old C57BL/6 mice (Ly5.1) were injected with 5-fluorouracil (5-FU) (150 mg/kg; SoloPak Laboratries, Inc., Elk Grove Village, Ill.) intra-peritoneally. Bone marrows were harvested on day 4 and centrifuged over NYCODENZ (1.077 mg/mL; Nycomed, Sweden). Light-density mononuclear cells (MNC) were collected from the interface and washed with Hank's Balanced Salt Solution supplemented with 5% FBS. Lin.sup.− Sca-1.sup.+c-Kit.sup.+ HSC were purified using standard procedures (Spangrude et al., 1995). Briefly, red cells were lysed in an ammonium chloride solution. The unlysed cells were then stained with optimized concentrations of antibodies against lineage markers CD2, CD3, CD5, CD8, CD19, CD11b, CD45R, Ly-6G, and TER119. Lineage marker-positive cells were depleted by 2 successive incubations with sheep anti-rat Ig-coupled magnetic beads (Dynal AS, Oslo, Norway). The Lin.sup.− cells were then stained with phycoerythrin (PE)-Sca-1 antibody and sorted using a FACSVANTAGE™ sorter (Becton Dickinson, San Jose, Calif.) using the enrichment mode. Dead cells were excluded from sorting and all analyses by gating on forward scatter and propidium iodide (PI; Molecular Probes, Eugene, Oreg.). The sorted Lin.sup.− Sca-1.sup.+ cells were re-stained with allophycocyaninconjugated anti-c-Kit antibody (APC-c-Kit; BD Pharmigen) and resorted using the normal mode. Lin.sup.− Sca-1.sup.+ c-Kit.sup.+ cells were sorted into a tube containing FBS. An aliquot of each sorted population was re-analyzed to verify purity before use.

Bone Marrow Co-Cultures.

Post-5-FU bone marrow MNC or CD3$^-$ NK1.1$^-$ post-5-FU bone marrow MNC ($2.5 \times 10^5$ per well) or Lin$^-$ Sca-1$^+$ c-Kit$^+$ cells ($10^4$ per well) were co-cultured with preformed monolayers of OP-9S/LXSN or OP-9S/LMJSN in 12-well plates in DME/30% FBS/$5 \times 10^{-5}$ M β-mercaptoethanol (β-ME), murine IL-7 (10 ng/mL; PeproTech, Inc., Rocky Hills, N.J.) and human Flt3L (15 ng/mL; R&D Systems, Minneapolis, Minn.). Half of the medium was changed every 2-4 days. To avoid crowding, one quarter to one half of the non-adherent cells were removed as needed at feeding.

Establishment and Subcloning of KIL.

KIL and 3 KIL-like cell lines were established from co-cultures of post-5-FU bone marrow MNC and OP-9S/LMJSN. These cultures were fed with the growth medium containing Flt3L and IL-7 only. No IL-2 was added at any point during the establishment of the cell line, since IL-2 induced terminal NK differentiation and the eventual demise of the co-cultures. NK precursors became the major cell type after about 6 weeks of co-culturing. Once NK or NK precursors became the dominant (>50%) cell type, other cells (mostly B progenitors and OP-9S) declined very rapidly, presumably due to the cytotoxicity and/or inhibitory cytokines of NK or NK precursors. KIL-like cell lines emerged after 3 months of continuous passaging in the same growth medium containing Flt3L and IL-7. Since OP-9S was the main source of SCF in the co-cultures, it was found to be beneficial to provide exogenous SCF (10-20 ng/mL; R&D Systems) after most OP-9S cells had been destroyed. Once established, KIL was found to be unresponsive to Flt3L. The cells were then maintained in DME/30% FBS/$5 \times 10^{-5}$ M β-ME, murine IL-7 (25 ng/mL) and murine SCF (50 ng/mL) and sub-cultured at 1:2-1:8 ratios every 2-3 days. As an alternative, the conditioned medium (10%; vol/vol) of the BHK/MKL cell line (Tsai et al. 1994) can be used as a source of SCF. KIL was sub-cloned by limiting dilution at ≤0.2 clonogenic cells per well in 96-well plates. The clonal lines were designated KIL C.1-C.5. To induce the terminal differentiation of KIL and KIL C.2, human IL-2 (Chiron, Emeryville, Calif.) was added at a final concentration of 20 ng/mL (with or without IL-7 or SCF). The medium was changed as needed.

Deposit of KIL Cell Line with American Type Culture Collection (ATCC).

A KIL cell line of the present invention (KIL C.2) was deposited on Mar. 30, 2005 at the ATCC depository and given accession number PTA-6651. The address of the ATCC is as follows:

American Type Culture Collection
P.O. Box 1549
Manassas, Va. 20108
United States of America KIL Growth Medium.

Iscove's Modified Dulbecco's Medium (IMDM) supplemented with heat-inactivated fetal bovine serum (FBS; 30%; vol/vol), L-glutamine (2 mM), beta-mercaptoethanol ($5 \times 10^{-5}$ M), penicillin (100 units/mL)/streptomycin (100 μg/mL)/Fungizone (0.25 μg/mL), recombinant murine stem cell factor (SCF, a.k.a c-kit ligand; 50 ng/mL; R&D Systems)

and recombinant murine IL-7 (25 ng/mL; R&D Systems). Incubate at 37° C. in 5% $CO_2$/95% air.

KIL Culturing Method.

Subculture at 1:4-8 ratios every three days by pipetting confluent cultures (ca. 4-6×$10^6$ cells per well) vigorously (more than 50% cells are adherent to the well). Retain the original wells since they contain many adherent cells. Transfer aliquots (each containing 0.5-1.0×$10^6$ cells) of the cell suspension to the original and additional wells and feed with fresh growth medium plus SCF and IL-7. Use 4-4.5 mL of medium per well in a 12-well plate (e.g., Falcon). Cultures set up in new wells may not be ready for sub-culturing for 4-6 days. If absolutely necessary, adherent KIL can be detached by a brief treatment with trypsin/EDTA after rinsing with phosphate-buffered saline twice.

Monoclonal Antibodies and Flow Cytometry.

Biotinylated monoclonal antibodies against NK1.1, Ly5.1, CD3, CD25, CD4, CD8, CD19, Mac-1, CD43, CD49b (DX5), CD51, CD94, B220, Fc Block (anti-CD16/CD32) and PE-conjugated monoclonal antibodies against T cell receptor .beta. chain (TCR.beta.) and TCR.gamma.delta. were purchased from BD Pharmingen (San Diego, Calif.). PE- or fluorescein isothiocyanate (FITC)-conjugated CD3, CD4, CD8, CD19, B220, Mac-1, Ly5.1 (clone A20), Ly6G (clone RB6-8C5) were generous gifts from Gerald Spangrude (Division of Hematology, University of Utah). Antibodies against murine granzyme B, perforin I and the carboxy terminus of human Notch-1 were purchased from Santa Cruz Biotechnology, Inc. (Santa Cruz, Calif.). Monoclonal antibody against NKG2D (clone A10) was kindly provided by Wayne Yokoyama (Howard Hughes Medical Institute, Washington University School of Medicine, St. Louis, Mo.). For flow cytometry, cells were incubated for 20 min. with optimal concentrations of PE- or FITC-conjugated or biotinylated antibodies and PI. Biotinylated antibodies were secondarily stained with PE- or FITC- or PerCP-streptavidin (SAv; Biomedia, Foster City, Calif.). Cells were analyzed using a FACSCAN™ (Becton Dickinson).

Northern and Western Analyses.

Total RNAs (5-10 .mu.g) were resolved on 1% formaldehyde agarose gels, blotted onto HYBOND™-N (Amersham Pharmacia Biotech, Inc. Piscataway, N.J.) and hybridized with .sup.32P-labeled probes at 65 .degree. C. in Rapid-Hyb buffer (Amersham Pharmacia Biotech, Inc.). Final washing was done in 0.1.times.SSC/0.1% SDS at 65 .degree. C. For Western analyses, protein lysates (5-10 .mu.g) were separated by denaturing sodium dodecyl sulfate-polyacrylamide (8%) gel electrophoresis, blotted onto IMMOBILON-P™ PVDF membrane (Millipore, Bedford, Mass.) and visualized by enhanced chemiluminescence. The production of rabbit serum against the intracellular domain of mJagged2 has been previously described (Tsai et al., 2000).

Nested PCR and Southern Hybridization.

The sequences of PCR primers used in detecting rearrangements in the TCRβ loci have been reported previously (King et al., 2002). In primary PCR, 0.5 μg genomic DNAs were amplified with the Dβ1.1ext/Dβ1.7ext or Dβ2.1ext/Dβ2.7ext primers for 30 cycles using the following cycling parameters: 94° C. for 30 sec., 59° C. for 1 min., 72° C. for 3 min. Two μL of the primary PCR reactions were re-amplified with the Dβ1.1int/Dβ1.7int or Dβ2.1int/Dβ2.7int primers for 30 cycles using the following cycling parameters: 94° C. for 30 sec., 63° C. for 40 sec., 72° C. for 2 min. 15 μL of the secondary PCR products were run on 2% agarose gels and stained with ethidium bromide. Southern blots of the PCR products were hybridized with $^{32}$P-labeled, gel-purified Dβ1.1-Dβ1.7 or Dβ2.1-Dβ1.7 fragments, whose sequences had been verified by direct sequencing.

Cytotoxicity Assay.

OP-9S cells (or NIH3T3 cells that had been irradiated with 900 rad) were seeded in 12-well plates and grown to confluence. One confluent monolayer of OP-9S or NIH3T3 was dissociated by trypsin and the cell number was determined. KIL was added to the confluent stromal layers at 1:1-4:1 effector-to-target ratios and fed with growth medium containing IL-7 and SCF. After 24-48 hours, non-adherent cells were removed and the cultures were gently rinsed with phosphate buffered saline, drained and stained with Coomassie blue stain (BioRad, Hercules, Calif.) for 30 min. After staining, the cultures were rinsed with tap water and air-dried.

Results

A major difference between T and NK cells is that while each T cell clone express only one type of T cell receptor, each NK cell clone expresses multiple NK receptors (activation, inhibitory and co-stimulatory) on the same cell (Kubota et al., 1999). In order to understand the intricate mechanisms controlling the activation or inhibition of NK cells, it is desirable to know the entire NK receptor repertoires of individual NK clones. However, unlike T or B cells, NK cell clones are extremely difficult to establish (Kubota et al., 1999; Karlhofer et al., 1995). To our knowledge, the KIL cell line described in this report is perhaps the only immortal NK cell line that has preserved most properties of its normal counterpart. As such, KIL provides a valuable system for NK research and therapeutic uses.

To demonstrate the present invention, a co-culture system different from that used to elucidate the function of Dll-1 was developed to investigate the role of mJagged2 (Tsai et al., 2000) in lymphoid development. In mouse embryos, mJagged2 expression is detected in thymus, dorsal aorta, paravertebral blood vessels, the basal layer of the entire epidermis, hair follicles, foregut, hindgut, brain and dorsal root ganglia (Shawber et al., 1996; Tsai et al., 2000; Felli et al., 1999; Luo et al., 1997). In newborn and adult mice, mJagged2 expression is detected in thymus, intestine, muscle, brain, testis, kidney, bone marrow, purified HSC, hematopoietic progenitors and endothelial cells (Shawber et al., 1996; Luo et al., 1997). However, little is known about its role in lymphopoiesis except that mice homozygous for a mutated mJagged2 (Jagged2$^{\Delta DSL/\Delta DSL}$) exhibit limb and craniofacial deformities, abnormalities in the thymic structure and altered Tαβ:Tγδ ratios (Jiang et al., 1998).

The co-culture system used in an embodiment of the present invention differs from the one described in the cited Dll-1 studies in three ways: First, a slow-growing variant of OP-9 (Kodama et al., 1994), designated as OP-9S, was used to allow prolonged co-cultivation and observation; Second, OP-9S was engineered to express mJagged2 rather than Dll-1; Third, IL-2 was added to half of the co-cultures at a certain point to promote complete differentiation of T and NK cells. The results show that mJagged2 has a strong stimulatory effect on the development of NK cells. Furthermore, NK precursors produced in the OP-9S/Jagged2 co-cultures continue to proliferate for 2-3 months, often resulting in the establishment of permanent NK precursor and/or NK cell lines, which have been extremely difficult to establish until now.

Jagged2 has a strong stimulatory effect on the development of NK cells in an environment that otherwise supports B cell development selectively (Schmitt et al., 2002; Schmitt et al., 2004; Carlyle et al., 1997). Different DSL ligands have nonredundant roles in lymphopoiesis (Jaleco et al., 2001). Thus, the invention provides for the ex vivo production of nascent NK cells, which are useful for both experimental and therapeutic purposes.

Based on the results of in vitro and in vivo studies, a model of NK cell development has been proposed (Yokoyama et al., 2004; Kim et al., 2002) in which HSCs give rise to common lymphoid progenitors (CLP) or common myeloid/lymphoid progenitors (CMLP), which upon further differentiation give rise to bipotent pT/NK. The bipotent pT/NK then give rise to either committed T progenitors (pT) or committed NK progenitors (pNK). While the concept of CLP or CMLP is still evolving (Kondo et al., 1997; Katsura et al., 2002), there is substantial evidence supporting the existence of the bipotent pT/NK (Carlyle et al., 1997; Ikawa et al., 1999). The differentiation of committed pNK to mature NK can be further divided into five stages based on cell surface markers and functionality (Yokoyama et al., 2004; Kim et al., 2002). Stage I is characterized by the expression of CD122 (IL-2/IL-15Rβ common chain) and the absence of most markers of NK cells including NK1.1 (in C57BL/6 mice), CD94, NKG2D and Ly49. The expression of NK1.1 and the NK receptors CD94/NKG2 and NKG2D marks the beginning of stage II. Stage III is distinguished by the expression of Ly49 (C-type lectin superfamily), c-kit (CD117) and additional markers. Stage IV is characterized by all markers present in stage III plus high levels of α2 integrin (CD49b) and low levels of cytotoxicity and interferon-γ (IFN-γ). Stage IV is also the stage when the developing NK cells undergo major population expansion. Stage V (mature NK) cells express high levels of the integrin Mac-1 α chain (CD11b), CD43 (leukosialin), cytotoxicity and IFN-γ (Spits et al., 1998).

Since the NK cells that developed in the OP-9S/LMJSN co-cultures were similar to the KIL cell line in all respects examined, the developmental stage of KIL provides useful information regarding the developmental stage of NK cells that appeared in the OP-9S/LMJSN co-cultures. Judging from the phenotypic profile of KIL (NK1.1$^+$ CD3$^-$ TCRαβ$^-$ TCRγδ$^-$ CD4$^-$ CD8$^-$ CD19$^-$ CD25$^+$ CD43$^+$ CD45$^+$ CD49b$^-$ CD51$^+$ CD94$^+$ NKG2D$^+$ Mac-1$^{-/low}$ B220$^-$ c-kit$^+$ perforin I$^+$ granzyme B$^+$ Notch-1$^+$) and the capacity of KIL to undergo extensive proliferation and differentiation in response to IL-2 (FIG. 6A), KIL is the equivalent of stage III/IV pNK. Taking into account the time it took for NK cells to develop in the OP-9S/LMJSN co-cultures (~2 weeks), the presumptive stage of KIL and the fact that Lin$^-$ Sca-1$^+$ c-Kit$^+$ HSC also generate NK cells when co-cultured with OP-9S/LMJSN (FIG. 2), it is believed that the target progenitors of Jagged2 may include stage I NK (CD122$^+$ NK1.1$^-$)/pNK, the bipotent pT/NK, CLP (or CMLP) and HSC (FIG. 7).

Figure 6:
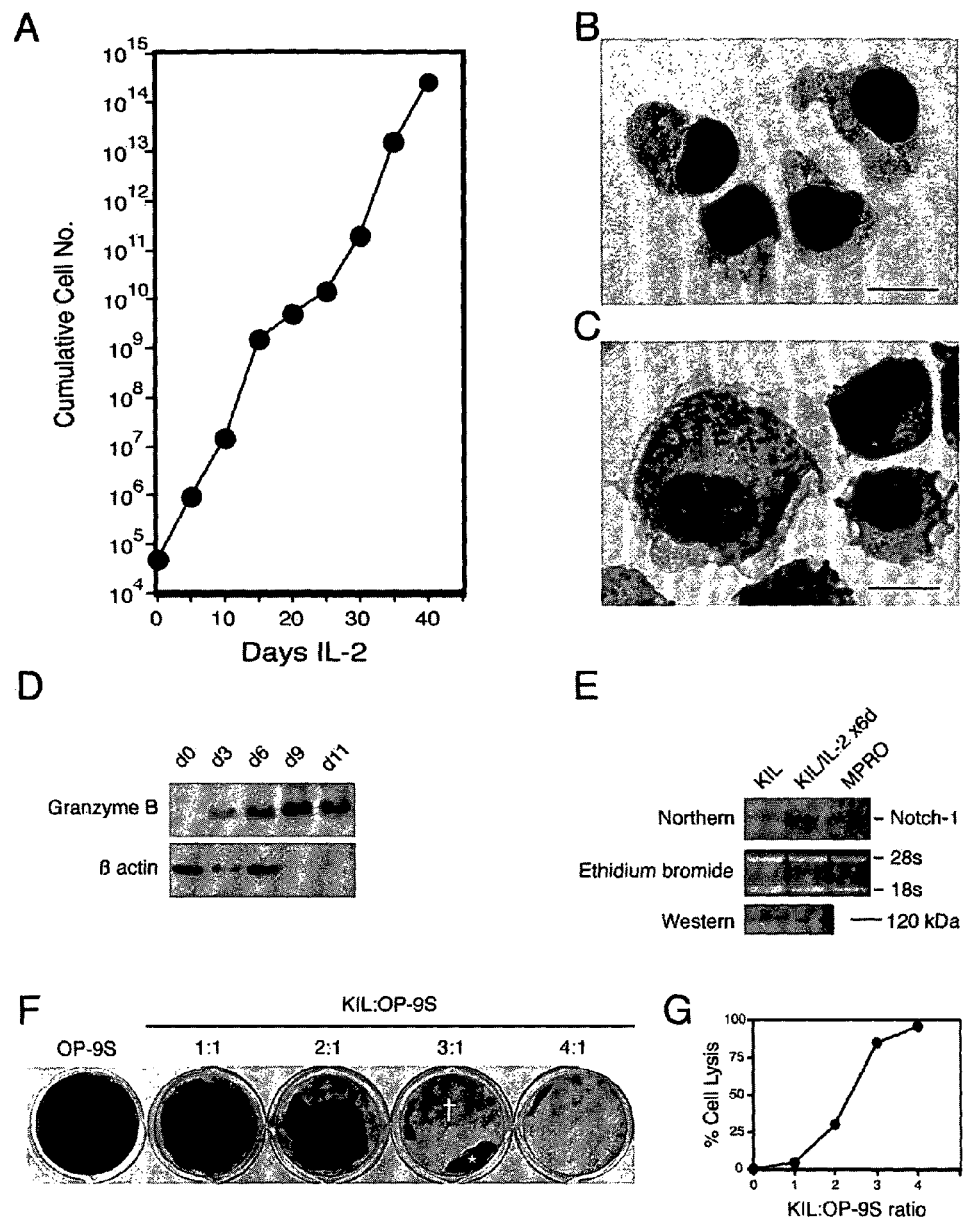
FIGS. 6A-6G shows that IL-2 induces further proliferation and differentiation of KIL.
Figure 7:
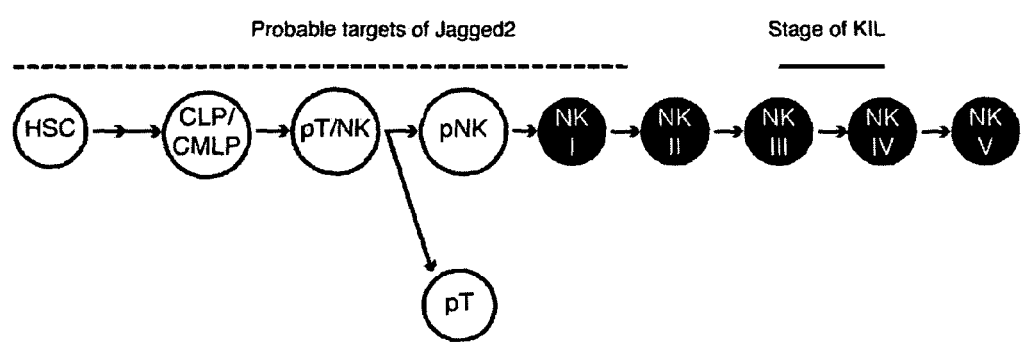
FIG. 7 illustrates the potential targets of Jagged2 regulation during NK cell development. The scheme depicts the differentiation of hematopoietic stem cell (HSC) to mature NK. CLP: common lymphoid progenitor (Kondo et al., 1997); CMLP: common myeloid/lymphoid progenitor (Katsura et al., 2002); pT/NK: bipotent progenitor for T and NK; pT: committed T progenitor; pNK: committed NK progenitor; NK I-V: stages of NK development as defined by Yokoyama and Kim (Yokoyama et al., 2004; Kim et al., 2002). Short dash: the equivalent stage of KIL. Dotted line: potential targets of mJagged2 regulation.

Northern and Western analyses revealed that KIL expressed significant levels of Notch-1 mRNA and protein with or without IL-2 stimulation (FIG. 6E). This raises the possibility that Jagged2 may have simply amplified pre-existing NK1.1$^+$ stage III/IV pNK in the OP-9S/LMJSN co-cultures. This scenario is rather unlikely for the following reasons: First, the kinetics of the appearance of CD3$^-$ NK1.1$^+$ NK cells in the OP9S/LMJSN co-cultures (~2 weeks) suggests the involvement of more primitive progenitors; Second, mJagged2 stimulated the development of NK cells from CD3$^-$ NK1.1$^-$ (double negative) post-5-FU bone marrow progenitors and the highly purified Lin$^-$ Sca-1$^+$ c-Kit$^+$ HSC (FIG. 2), both of which were depleted of NK1.1$^+$ progenitors; Third, sorted CD3$^-$ NK1.1$^+$ post-5-FU bone marrow MNC failed to proliferate under the same co-culture conditions; Finally, neither sorted Lin$^-$ Sca-1$^+$ c-Kit$^+$ HSC nor CD3$^-$ NK1.1$^-$ post-5-FU bone marrow progenitors proliferated in response to IL-2 alone.

To study the effects of mJagged2 on NK cell development, a slow-growing variant of the OP-9 cell line was derived, designated as OP-9S, to minimize metabolic competition during prolonged co-cultivation with bone marrow progenitors. The original OP-9 stromal cell line was derived from a B6C3F1 mouse with osteopetrosis (Kodama et al., 1994). It does not express macrophage-colony stimulating factor. OP-9S was transduced with retroviral vectors LXSN (negative control) and LMJSN (expressing full-length mJagged2) and selected with G418. The resultant cell lines are referred to as OP-9S/LXSN and OP-9S/LMJSN, respectively. Northern and Western analyses confirmed the expression of the full-length mJagged2 in OP-9S/LMJSN, but not OP-9S/LXSN (FIG. 1A).

To study the effects of mJagged2 on lymphoid development, light-density (<1.077 g/ml) mononuclear cells (MNC) from post-5-fluorouracil (post-5-FU) murine bone marrows were co-cultured with pre-established monolayers of OP-9S/LXSN and OP-9S/LMJSN in the presence of murine IL-7 (10 ng/mL) and Flt3L (15 ng/mL). To minimize contribution from mature NK or T cells, we used young C57BL/6 (Ly5.) mice that were only 4-6 weeks old. In the first 6-9 days of co-culturing, the proliferating cells were mostly small, round lymphoblasts. Around day 9, some racket-shaped cells began to appear in the OP-9S/LMJSN co-cultures and to a much lesser extent in the control OP-9S/LXSN co-cultures and correlated with the appearance of CD3$^-$ NK1.1$^+$ cells. To stimulate further development of such cells, human IL-2 (25 ng/mL) was added to half of the co-cultures on day 10. In the next 5-9 days, more racket shaped cells emerged in the IL-2-stimulated OP-9S/LMJSN co-cultures. Flow cytometric analyses on day 19 of co-cultivation showed that many cells (~36%) in the IL-2-treated OP-9S/LMJSN co-cultures were CD3$^-$ NK1.1$^+$ NK cells (FIG. 1B). Such cells were extremely rare (~0.04%) in IL-2-stimulated OP-9S/LXSN co-cultures (FIG. 1B). Wright-Giemsa staining of sorted CD3$^-$ NK1.1$^+$ cells revealed that they were large granular lymphocytes containing azurophilic granules.

Calculations based on the total cell numbers and the percentages of CD3$^-$ NK1.1$^+$ cells showed that the absolute numbers of CD3$^-$ NK1.1$^+$ NK cells in the OP-9S/LMJSN co-cultures were 160 times greater than in the control OP-9S/LXSN co-cultures when IL-2 was added on days 10-19. Without IL-2, the absolute numbers of CD3$^-$ NK1.1$^+$ NK cells in the OP-9S/LMJSN co-cultures were still 13 times greater than those in the negative control group. Taken together, these findings suggest that mJagged2 in combination with OP-9S, IL-7 and Flt3L stimulated the development of NK precursors, which underwent further proliferation and differentiation in response to IL-2. To examine the effects of delayed IL-2 addition, the addition of IL-2 was withheld until day 20 of co-cultivation. Flow cytometry was then performed on day 28. The results again showed much higher frequencies (~35%) of CD3$^-$ NK1.1$^+$ NK cells in the OP-9S/LMJSN co-cultures than the control OP-9S/LXSN co-cultures (~0.22%)(FIG. 1C). The remaining cells were mostly CD19$^+$ B220$^+$ or CD19$^-$ B220$^+$ B lymphoid precursors (FIG. 1C, bottom panels).

To examine the ability of mJagged2 to induce NK cell development from primitive hematopoietic progenitors, Lin$^-$ Sca-1$^+$ c-Kit$^+$ bone marrow progenitors were purified by a combination of magnetic bead depletion of lineage marker-positive cells and fluorescence-activated cell sorting (FACS).

Figure 2:
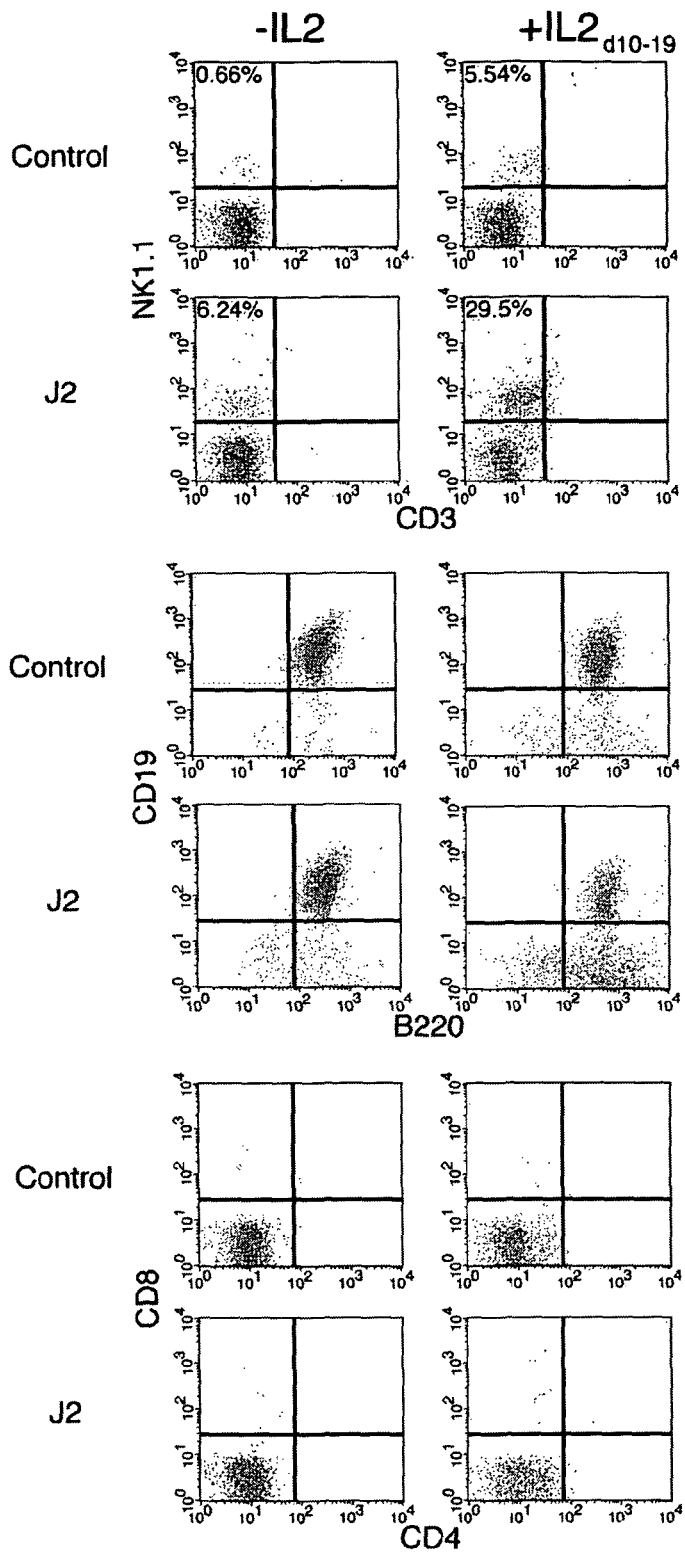
FIG. 2 shows that Jagged2 induces the development of NK cells from Lin$^-$ Sca-1$^+$ c-Kit$^+$ HSC. Lin$^-$ Sca-1$^+$ c-Kit$^+$ HSC were co-cultured with OP-9S/LXSN (negative control) or OP-9S/LMJSN ("J2") in the presence of IL-7 and Flt3L for 19 days with or without IL-2 on days 10-19 and analyzed for the expression of NK1.1 vs. CD3, CD19 vs. B220 and CD8 vs. CD4. The percentage of CD3$^-$ NK1.1$^+$ cells (left upper quadrant) is indicated.

The Lin⁻ Sca-1⁺ c-Kit⁺ fraction is highly enriched for HSC (Spangrude et al, 1995). Lin⁻ Sca-1⁺ c-Kit⁺ cells were co-cultured with OP-9S/LXSN or OP-9S/LMJSN in the presence of IL-7, and Flt3L. IL-2 was added to half of the co-cultures on day 10. Flow cytometry was performed on day 19 of co-cultivation. Again, significantly more CD3⁻ NK1.1⁺ NK cells developed in OP-9S/LMJSN co-cultures (~30%) than in the control co-cultures (~5%) (FIG. 2). The absolute numbers of CD3⁻ NK1.1⁺ NK cells in the OP-9S/LMJSN co-cultures were 7.5-fold higher than those in the negative control group. Virtually no CD4⁺ or CD8⁺ cells were detected (FIG. 2, bottom panels), indicating that mJagged2 had no stimulatory effect on T cell development.

The CD3⁻ NK1.1⁺ NK cells that developed in the co-cultures of post-5-FU bone marrow MNC and OP-9S/LMJSN exhibited extensive proliferative capacity. They continued to proliferate as long as fresh media, IL-7, and Flt3L were provided every 2-4 days. After 2-3 months, they became the predominant cell type. In contrast, the control OP-9S/LXSN co-cultures remained dominated by CD19⁺ B220⁺ or CD19⁻ B220⁺ B lymphoid precursors. Multiple spontaneously immortalized NK precursor cell lines emerged from the OP-9S/LMJSN (but not OP-9S/LXSN) co-cultures after 3 months. The prototype is designated as KIL, for Killer Lymphocyte. To confirm the immortalization of KIL, the cell line has been continuously cultured henceforth.

Figure 3:
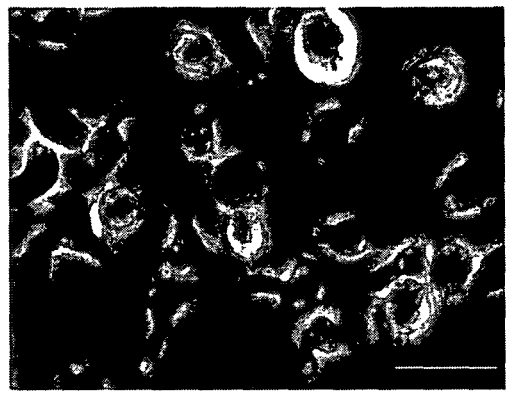
FIGS. 3A-3C show the morphology and growth factor responses of KIL.
Figure 3:
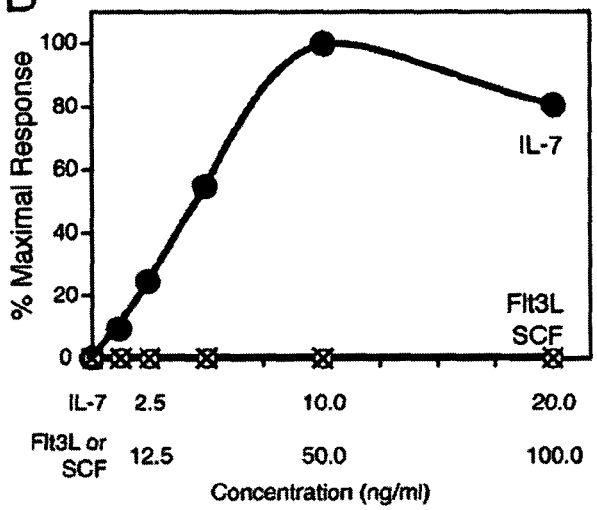
Figure 3:
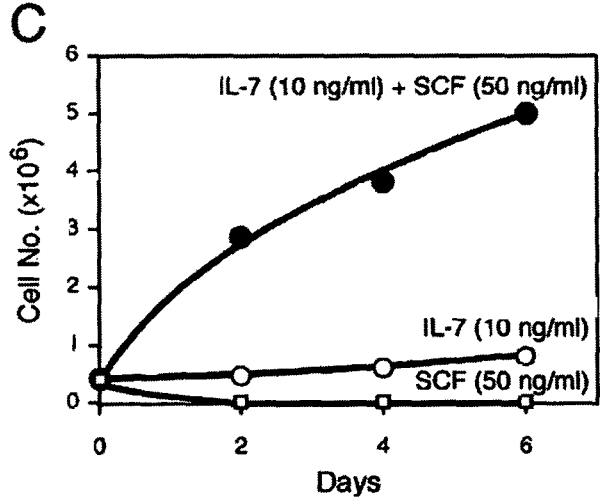
Figure 4:
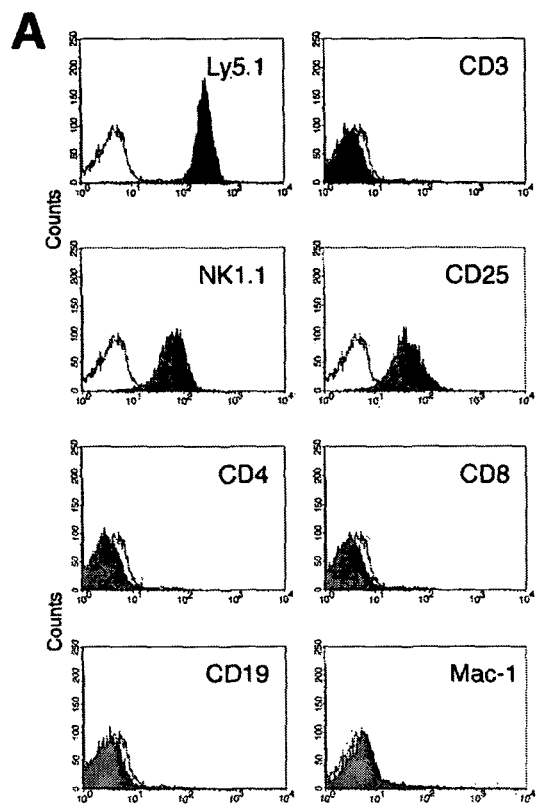
FIGS. 4A-4C show the phenotypic markers of the KIL cell line.
Figure 4:
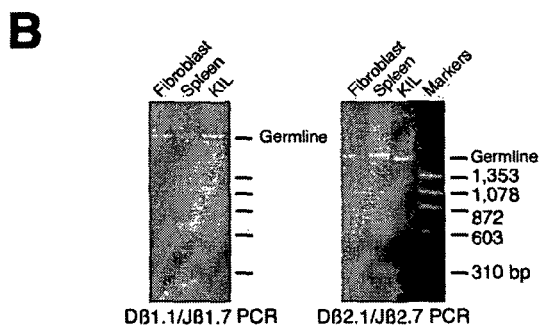
Figure 4:
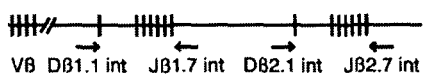
Figure 4:
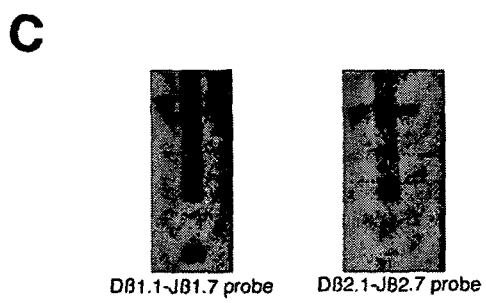

Under phase-contrast microscopy, KIL displayed the characteristic racket shape at 37° C. (FIG. 3A), but a spherical shape at room temperature suggesting that maintaining the racket shape requires energy. The survival and proliferation of KIL depends on IL-7. In the absence of IL-7, KIL becomes apoptotic within 24 hours (FIG. 3B). KIL cannot survive with SCF or Flt3L alone but SCF synergizes with IL-7 in stimulating the proliferation of KIL (FIGS. 3B&C). Flow cytometry demonstrates that KIL expresses CD45 (Ly5.1), CD25 (IL-2 receptor a chain) and NK1.1 (NKR P1C receptor), but not CD3, CD4, CD8, CD19 (FIG. 4A), B220, TCRαβ or TCRγδ (not shown). Less than 1% of the KIL express Mac-1 (FIG. 4A). Like normal NK cells, the TCRαβ loci of KIL remain in the germline configuration (FIGS. 4B&C). On Wright-Giemsa-stained cytospin preparations, KIL appears as large granular lymphocytes with fine azurophilic cytoplasmic granules (see FIG. 6B).

Figure 5:
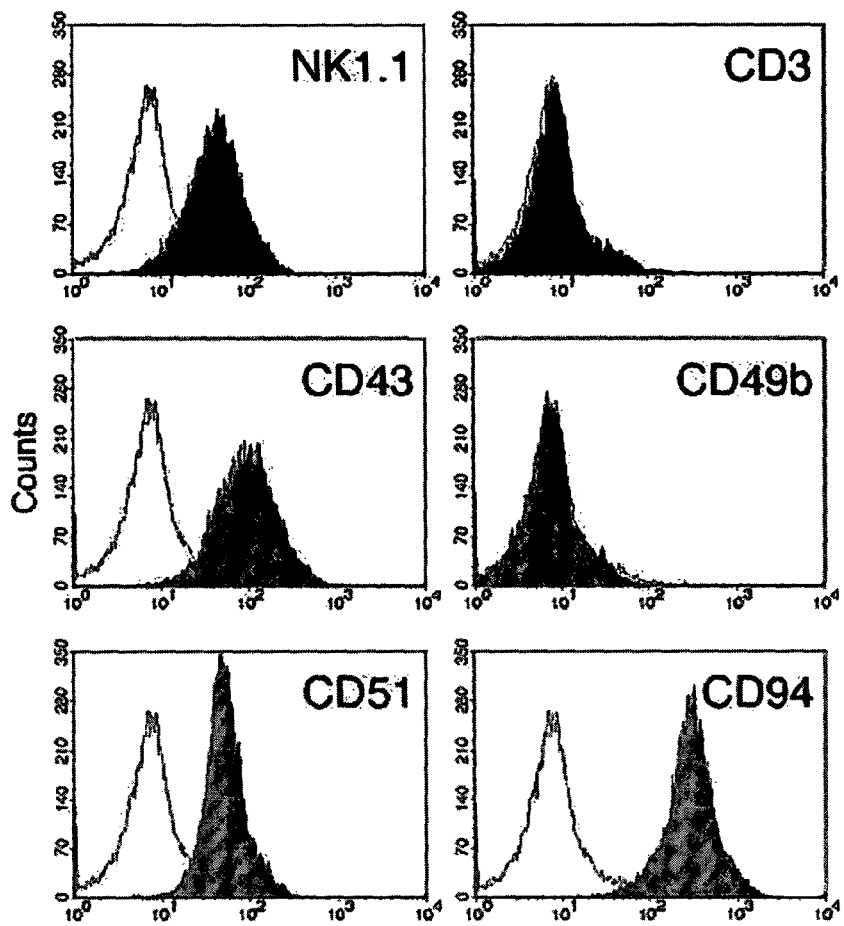
FIG. 5 illustrates the cell surface markers of the KIL C.2 clone. In addition to those shown here, KIL C.2 displays all the phenotypic markers of the parental KIL as shown in FIG. 4A. Thin line: isotype control.

Five clonal lines of KIL, designated KIL C.1 to C.5, were obtained by limiting dilution. KIL C.2 was chosen as the prototype because it had a shorter doubling time. KIL C.2 is very similar to the uncloned KIL in every respect examined, including morphology, growth factor responsiveness, cell surface markers and cytotoxicity (described herein). The KIL C.2 cell line was deposited with the ATCC on Mar. 30, 2005 and given the accession number PTA-6651. In addition to all surface markers shown in FIG. 4A, both KIL C.2 and the parental KIL also express CD43, CD51 and CD94 (FIG. 5) and NKG2D.

When stimulated by IL-2 alone, KIL proliferated extensively over a period of 5-6 weeks, during which the cell number increased by ~$10^{10}$-fold (FIG. 6A). Thereafter, proliferation ceased and all terminally differentiated NK cells disintegrated. The culture then became extinct. Serial phase-contrast microscopy revealed that KIL became larger and very adherent to the tissue culture dishes after 4-6 days of stimulation with IL-2. Wright-Giemsa staining of KIL that had been stimulated with IL-2 for 6 days showed that the KIL cells contained numerous large azurophilic granules, cytoplasmic vacuoles and ruffled cell membranes (FIGS. 6B&C). Western analysis showed that granzyme B was up-regulated by at least ten-fold in KIL stimulated with IL-2 for 6-9 days (FIG. 6D). KIL expressed perforin I by Western analysis as well as Notch-1 by Northern and Western analyses with or without IL-2 stimulation (FIG. 6E).

It was observed that the emergence of CD3⁻ NK1.1⁺ NK cells in the OP-9S/LMJSN co-cultures was accompanied by destruction of the OP-9S cells. This temporal linkage suggested that the emerging NK cells were cytotoxic to the OP-9S cells. To examine the cytolytic activity of KIL against OP-9S, KIL cells were added to monolayers of OP-9S stromal fibroblasts at various ratios in growth medium containing IL-7 and SCF. Phase-contrast microscopy revealed the presence of microscopic cytolytic foci in the OP-9S monolayers within 12 hours of the addition of KIL (or KIL C.2). After 24-48 hours, large areas of the OP-9S monolayers were denuded (FIG. 6F). The degree of cytolysis correlated with effector-to-target cell ratios (FIG. 6G). Similar findings were made using NIH3T3 stromal fibroblasts that had been sub-lethally irradiated (900 rad) to prevent rapid re-growth. Attempts at the more traditional chromium-51 release assay were complicated by the strong tendency of the activated KIL to adhere to the tissue culture dishes and their ability to re-uptake chromium-51 released by the lysed target cells during the assay period. The cytotoxicity assay described herein is more robust and more easily performed than the traditional chromium-51 release assay. It is also less hazardous as no radioisotopes are used. In addition, the fibroblast-based cytotoxicity assay provides a permanent visual record. Regardless of the assay method, the results clearly demonstrate that KIL is cytotoxic.

The cytotoxicity of KIL cells is further demonstrated by using pathogen-free female and male CB-17 IcrHsd scid/scid (SCID/beige, BALB/c) mice that are obtained from an animal breeding colony and provided food and water ad liben. A single-cell suspension of exponentially growing human CX2 tumor cells (about $2.5 \times 10^6$ in sterile media) is injected into the intraperitoneal cavity of the mice. On days 1, 2, 4, and 8 after tumor cell inoculation, ex vivo expanded KIL cells, preferably obtained from mice having the same or similar HLA type as the test subjects, are injected intravenously. The in vivo cytolytic activity of the KIL cells is determined on day 21 after intraperitoneal injection of tumor cells. The complete body weight of each mouse is determined and the complete tumor is excised from the intraperitoneal cavity with a scalpel under sterile conditions. The weight of each individual tumor is determined, separately.

Mice treated with KIL cells are found to have reduced tumor size relative to control animals.

In one aspect of the invention, cells of the NK cell lineage are generated from HSCs. HSCs can be from a newborn mammal, a juvenile mammal, or an adult mammal. Preferred mammals include, for example, humans, non-human primates, pigs, cows, horses, dogs, cats, mice and rats, They can be derived from bone marrow, blood, umbilical cord, fetal tissue and other sources known in the art. HSCs may be obtained from a sample taken from a subject for use in a treatment. In a particular embodiment, HSCs are obtained from bone marrow.

Hematopoietic progenitor cells and/or embryonic stem cells are cultured in a system of the invention to form cells of the NK precursor, NK and/or KIL cell line. The cells are cultured in the presence of one or more Notch receptor ligand, such as hJagged2, for a sufficient time to form cells of the NK precursor, NK and/or KIL cell line.

In an embodiment, the hematopoietic progenitor cells or embryonic stem cells are cultured in a 6 cm or 10 cm tissue culture-treated dish with feeder cells expressing a Notch receptor ligand. The feeder cells may also provide one or more additional factor(s), e.g., IL-7, Flt3L and/or SCF. In a particular embodiment, hematopoietic progenitor cells are cultured on a monolayer of OP-9S cells expressing Jagged2.

One or more positive cytokines that promote commitment and differentiation of cells of the NK cell lineage may also be added to the culture. The cytokines may be human in origin, or may be derived from other species. The concentration of a cytokine in a culture is typically about 1-20 ng/mL. The following are representative examples of cytokines, growth factors and/or ligands that may be employed in the present invention: all members of the interleukin family including, but not limited to IL-7 and/or IL-2, Flt3L, and growth factors, including but not limited to, SCF. Preferably the cytokines used herein are Flt3L and IL-7. The cytokines may be used in combination with equal molar or greater amounts of a glycosaminoglycan such as heparin sulfate. The cytokines are commercially available or can be produced by recombinant DNA techniques and purified to various degrees. Some of the cytokines may be purified from culture media of cell lines by standard biochemical techniques.

The cells of the invention, e.g., HSC, NK precursor, NK and/or KIL, may be cultured in culture medium comprising conditioned medium or non-conditioned medium. Examples of suitable conditioned medium include Iscove's Modified Dulbecco's Medium (IMDM), DMEM, or α-MEM, conditioned with stromal cells such as OP-9S/LMJSN, for example containing Flt3L, IL-7 and/or SCF. Examples of suitable non-conditioned medium include IMDM, DMEM, or α-MEM, or equivalent medium. The culture medium may comprise serum (e.g., bovine serum, fetal bovine serum, calf bovine serum, horse serum, human serum, or an artificial serum substitute) or it may be serum free.

The culture conditions entail culturing the HSCs for a sufficient period of time so that cells in the preparation form precursor NK cells, NK and/or KIL cells. The cells are maintained in culture generally for 40-100 days, preferably 60 to 95 days. It will be appreciated that the cells may be maintained for the appropriate amount of time required to achieve a desired result, i.e., a desired cellular composition. For example, to generate a cellular composition comprising primarily NK cells, the cells may be maintained in culture for about 35 to 45 days. NK cells may be maintained in culture for 60 to 95 days to generate a cellular composition comprising KIL cells.

The methods of the present invention lead to newly created cellular compositions comprising high levels of NK precursor, NK and/or KIL cells. The resulting NK cellular precursors and/or NK cellular compositions exhibit, or have the potential to differentiate into cells that exhibit morphological, physiological, functional, and/or immunological features of NK cells. The cells in the resulting cellular compositions were also characterized by expression of NK cell markers.

A cellular composition resulting from a method of the invention may comprise one or more of the following NK cells and progenitor or precursor cells committed to the formation of NK or KIL cells;

(a) $CD3^-$, $NK1.1^+$ cells;
(b) $CD45^+$, $CD25^+$, $NK1.1^+$ cells;
(c) $CD45^+$, $CD25^+$, $NK1.1^+$, $CD43^+$, $CD51^+$, $CD94^+$, $NKG2D^+$ cells;
(d) $NK1.1^+$, $CD3^-$, $TCR\alpha\beta^-$ and/or $TCR\gamma\delta^-$, $CD4^-$, $CD8^-$, $CD19^-$, $CD25^+$, $CD43^+$, $CD45^+$, $CD49b^-$, $CD51^+$, $CD94^+$, $NKG2D^+$, $Mac-1^{-/low}$, $B220^-$, $c-kit^+$, perforin $I^+$, granzyme $B^+$, $Notch-1^+$ cells;
(e) NK cells that are $CD3^-$, $NK1.1^+$;
(f) NK cells that are $CD3^-$, $NK1.1^+$, $CD4^-$, and $CD8^-$.

In aspects of the invention, a cellular composition comprises (a); (a) and (b); (a) (b) and (c); (a), (b), (c), and (d); (a), (b), (c), (d), and (e); or (a), (b), (c), (d), (e) and (f).

The cells in a cellular composition generated in accordance with the invention may be separated to obtain populations of cells largely consisting of one or more types of NK precursor, NK and/or KIL cells. Cells can be separated using standard techniques based on the expression of one or more phenotypic or physiological characteristic. Selection methods known in the art, negative and/or positive selection, may be used for the enrichment of HSCs. For example, cells can be sorted based on cell surface antigens using a fluorescence activated cell sorter, or magnetic beads. Negative selection columns can be used to remove cells expressing lineage specific surface markers. Positive selection using antibodies to identify NK precursor, NK and/or KIL cell specific cell surface markers, or negative selection using non-NK precursor, non-NK and/or non-KIL cell specific markers (e.g., markers specific for T cells) may be employed. For example, KIL cells can be screened for expression of specific markers such as $CD45^+$, $CD25^+$, $NK1.1^+$, $CD43^+$, $CD51^+$, $CD94^+$ and $NKG2D^+$ using techniques such as flow cytometric cell sorting. Standard assay systems may also be used to identify functional NK precursor, NK and/or KIL cells.

Cell preparations comprising cells of an HSC cell line may be induced into NK precursor, NK and/or KIL cells in vitro, in vivo, and/or ex vivo. This may be accomplished in vitro/ex vivo by separating the HSCs (e.g., $Lin^-$ $Sca-1^+$ $c-kit^+$ cells) culturing the cells in the presence of a Notch receptor ligand or system as described herein, or culturing in an intact organ system (e.g., thymic organ culture). After differentiation of the cells into NK precursor, NK and/or KIL cells, the cells may be separated to obtain a population of cells largely consisting of NK precursor, NK and/or KIL cells. NK precursor cells, optionally arising from HSCs isolated from a subject and the population expanded ex vivo, may be administered to a subject in vivo and allowed to differentiate into NK cells. Likewise, NK cells of the invention may be administered to a subject.

The methods of the invention also provide expanded populations of NK precursor, NK and/or KIL cells (e.g., NK cells that are $CD3^-$ and $NK1.1^+$). Using a method of the invention it is possible to increase the number of NK cells that are $CD3^-$ and $NK1.1^+$ by 160 fold, compared to the negative OP-9S/LXSN and post-5-fluorouracil mononuclear cell co-culture, through adding IL-2 on days 10-19 to the OP-9S/LMJSN and post-5-fluorouracil mononuclear cells co-culture. Even without adding IL-2 to the co-cultures, the resulting increase in the number of NK cells that are $CD3^-$ and $NK1.1^+$ over the negative control OP-9S/LXSN co-culture is about 13 fold.

Further expanded populations of KIL cells may be accomplished through culturing the HSCs (e.g., $CD3^-$ and $NK1.1^+$ NK cells) for 3 months. The HSCs (e.g., $CD3^-$ and $NK1.1^+$ NK cells) proliferate as long as fresh media, IL-7 and Flt3L are provided every 2-4 days.

Multiple spontaneously immortalized $CD3^-$ and $NK1.1^+$ NK cell lines emerge after 3 months of culturing. These KIL cells are maintained in continuous culture by adding IL-7 and SCF to the media.

Cellular compositions comprising NK precursor, NK and/or KIL cells generated using the methods of the invention may be genetically modified (transduced or transfected) either in nature or by genetic engineering techniques in vivo or in vitro. Cells can be modified by introducing mutations into genes of the cells or by introducing transgenes into the cells. Insertion or deletion mutations may be introduced in a cell using standard techniques. A gene encoding a selectable marker may also be integrated into the cells.

A polynucleotide encoding a protein, for example, Jagged2, may be introduced into cells by conventional techniques known in the art. Such techniques include, but are not limited to, calcium phosphate or calcium chloride co-precipitation, DEAE-dextran-mediated transfection, lipofection, electroporation, viruses (e.g., replication defective retroviruses, adenoviruses and adeno-associated viruses) or microinjection. By way of example, a polynucleotide encoding mJagged2 was introduced into cells, as shown herein, using an appropriate viral vector. As will be recognized by a person of ordinary skill in the art, an expression vector typically contains appropriate regulatory sequences, and may contain additional genes or nucleic acid sequences, such as reporters and/or selectable markers.

An aspect of the present invention relates to genetically engineering NK precursor, NK and/or KIL cells in such a manner that the cells or cells derived therefrom produce, in vitro or in vivo, polypeptides, hormones and proteins not normally produced in the cells in biologically significant amounts, or produced in small amounts but in situations in which increased expression, either regulated or constitutive, would lead to a therapeutic benefit. For example, the cells may be engineered with a gene that expresses a cytokine which increases the activity of NK cells towards a specific tumor (Konstantinidis et al., 2005). Alternatively, the cells can be modified such that they produce a recombinant molecule such as a protein; and the recombinant protein can be purified from the cells. Proteins produced in NK precursor, NK and/or KIL cells may be secreted into the surrounding media or purified from the cells. The expression of the recombinant molecule could be in vivo as part of a therapy or the expression of the recombinant molecule could be used to make a protein in vitro. The cells formed in this way can serve as continuous short term or long term production systems of the expressed substance.

Thus, in accordance with this aspect of the invention, NK precursor, NK and/or KIL cells in cellular compositions generated using the methods of the invention can be modified with genetic material of interest. The modified cells can be cultured in vitro under suitable conditions so that they are able to express the product of the gene expression or secrete the expression product. These modified cells can also be administered in vivo so that the expressed product will have a beneficial effect in a subject.

In addition, NK precursor, NK and/or KIL cells may also be modified to reduce or eliminate expression of a gene product. For example, the cells may be modified to express siRNA or may be modified to introduce a mutation into a gene. As will be recognized by a person of ordinary skill in the art, the cells of the invention may also have increased expression of one gene or gene product and decreased expression of another gene or gene product. Hence, for the sake of brevity, much of the discussion herein focuses on increased expression of a gene, however, it is to be understood that any such discussion also includes increased or decreased expression of any desirable sequence, including, but not limited to, siRNA, antisense constructs, and fragments of a gene or gene product.

In one embodiment, cells of the precursor NK, NK and/or KIL cell lines are genetically engineered with an inducible gene that encodes a recombinant molecule that upon expression leads to the programmed cell death (apoptosis) of the precursor NK, NK and/or KIL cell. The inducible apoptosis of the precursor NK, NK and/or KIL cell may be used as a means to control the application of particular embodiments of the invention. For example, a KIL cell line targeted to a particular tumor may be introduced into a patient with said tumor. After proliferation of the KIL cell line and the consequent destruction of the tumor, the KIL cell line can be triggered to enter apoptosis through induction, in vivo, of the engineered apoptotic gene.

In a further embodiment, transduced precursor NK cells with the potential to form NK cells can be induced in vivo and/or in vitro to differentiate into NK cells that will express the gene product. The cells may be administered in a mixture with other cells or separately and may be delivered to a target area, e.g. by intratumor injection, or the cells may be introduced intravenously and allowed to naturally migrate to a target area. Thus, genes can be introduced into cells which are then injected into a recipient where the expression of the gene will have a therapeutic effect.

The technology may be used to produce additional copies of desirable genes to allow augmented expression by NK precursor, NK and/or KIL cells of certain gene products in vivo and/or in vitro. These genes can be, for example, hormones, matrix proteins, cell membrane proteins, and cytokines.

The NK precursor, NK and/or KIL cell lines that comprise cells generated using the methods of the invention can be used in a variety of methods (e.g., transplantation) and have numerous uses in the field of medicine.

Transplantation, as used herein, can include the steps of isolating a cellular composition comprising cells of the NK precursor, NK and/or KIL cell lines according to the invention and transferring said cells in the composition into a mammal or a patient. Transplantation can involve transferring the cells into a mammal or a patient by injection of a cell suspension into the mammal or patient, surgical implantation of a cell mass into a tissue or organ of the mammal or patient, or perfusion of a tissue or organ with a cell suspension. The route of transferring the cells may be determined by the requirement for the cells to reside in a particular tissue or organ and by the ability of the cells to find and be retained by the desired target tissue or organ.

In an aspect of the invention, the newly created cellular compositions comprising cells of the NK precursor, NK and/or KIL cell line, and cellular compositions differentiated therefrom (e.g., mature KIL cells), can be used in both cell therapies and gene therapies aimed at alleviating disorders and diseases, in particular those involving tumors and/or viral infections.

The cell therapy approach involves transplantation of NK precursor, NK and/or KIL cell line(s) as a treatment for diseases. The steps in this application include: (a) producing a cellular composition comprising cells of the NK precursor, NK and/or KIL cell line, or a cellular composition comprising cells differentiated therefrom, as described herein; and (b) allowing the cells to form functional connections either before or after a step involving transplantation of the cells. The cell therapy may also involve transfecting the cells with an appropriate vector, e.g., cDNA, encoding a desired protein, followed by a step where the modified cells are transplanted.

Thus, the cellular compositions with cells of the NK precursor, NK and/or KIL cell line or cells differentiated therefrom, can be used to replace and/or augment NK cells in a patient in a cell therapy approach, which is useful in the treatment of diseases. These cells can be also used as vehicles for the delivery of specific gene products to a patient.

The invention also provides a method of treating a patient with a condition involving NK precursor and/or NK cell lines or requiring replacement of NK precursor and/or NK cells comprising transferring a cellular composition comprising cells of the NK precursor, NK and/or KIL cell line into the patient. For example, conditions such as preleukemias, myeloproliferative disorders, leukemia of various types, aleukemic leukemia, plasmacytosis, plasmacytoma, multiple myeloma, Hodgkin lymphoma and non-Hodgkin lymphoma.

Another aspect of the invention is a kit for producing cellular compositions comprising cells of the NK precursor, NK and/or KIL cell lines, preferably the KIL cell line. The kit includes the reagents for implementing a method or system of the present invention. Preferably, the kit is a KIL cell line, optionally with vectors and other components necessary for transfection, transformation and/or transduction, as well as instructions for using said kit, e.g., to transfect, transform, and/or transduce the included KIL cell line with a nucleic acid sequence encoding for a recombinant molecule of interest.

The cellular compositions comprising cells of the NK precursor, NK and/or KIL cell lines may be used to screen for potential modulators or therapeutics that modulate development or activity of cells of the NK precursor, NK and/or KIL cell lines or cells differentiated therefrom. In particular, the cellular compositions may be subjected to a test substance, and the effect of the test substance may be compared to a control (e.g., in the absence of the substance) to determine if the test substance modulates development or activity of cells of the NK precursor, NK and/or KIL cell lines or cells differentiated therefrom.

In an embodiment of the invention, a method is provided for using a cellular composition of the invention comprising cells of the NK precursor, NK and/or KIL cell lines or cells differentiated therefrom to assay the activity of a test substance comprising the steps of:

(a) generating cells of the NK precursor, NK and/or KIL cell lines with a system or method of the invention in the presence of a test substance, or culturing cells of NK precursor, NK and/or KIL cell line compositions using a system or method of the invention in the presence of a test substance; and (b) detecting the presence or absence of an effect of the test substance on the survival of the cells or on a morphological, functional, and/or physiological characteristic and/or molecular biological property of said cells, whereby an effect altering cell survival, a morphological, functional, and/or physiological characteristic and/or a molecular biological property of the cells indicates the activity of the test substance.

In another aspect of the invention, a method is provided for using cells of the NK precursor, NK and/or KIL cell lines, or cells differentiated therefrom and generated in accordance with the invention, to screen a potential new drug to treat a disorder susceptible to NK precursor cells and/or NK cells comprising the steps of:

(a) generating cells of the NK precursor, NK and/or KIL cell lines with a system or method of the invention in the presence of a potential new drug, or culturing cells of NK precursor, NK and/or KIL cell line preparations generated using a system or method of the invention in the presence of a potential new drug; and (b) detecting the presence or absence of an effect of the potential new drug on the survival of the cells in vivo and/or in vitro or on a morphological, functional and/or physiological characteristic and/or molecular biological property of said cells, whereby an effect altering cell survival, a morphological, functional, and/or physiological characteristic and/or a molecular biological property of the cells in vivo and/or in vitro indicates the activity of the potential new drug.

The cellular compositions of the invention may be used to prepare model systems of disease. The cellular compositions of the invention can also be used to produce growth factors, hormones, cytokines, enzymes, and/or any molecule of interest.

The cellular compositions of the invention can be used to screen for genes expressed in or essential for differentiation of NK precursor, NK and/or KIL cell lines. Screening methods that can be used include Representational Difference Analysis (RDA) or gene trapping with, for example, SA-lacZ (Hill et al., 1993). Gene trapping can be used to induce dominant mutations (e.g., by deleting particular domains of the gene product) that affect differentiation or activity of NK precursor, NK and/or KIL cell lines and allow the identification of genes expressed in, or essential for, differentiation of these cells.

The cellular compositions of the invention may be used to study the cell biology of NK precursor, NK and/or KIL cell lines.

The cellular compositions and expanded cellular compositions of the invention comprising increased numbers of cells of the NK precursor, NK and/or KIL cell lines may be used for enhancing the immune system of a patient.

The cellular compositions may facilitate enhancement or reconstitution of the patient's immune system. The cellular compositions of the NK precursor, NK and/or KIL cell lines may be used to facilitate the destruction of targeted cells which include, but are not limited to, leukemia, lymphomas or other cancers.

In an aspect of the invention, the cellular compositions are used in the treatment of leukemia, lymphomas, and/or other cancers in which other treatments or the disease have resulted in the depletion of NK precursor and/or NK cells. For example, a cellular composition of the invention is used to treat subjects infected with HIV-1 that have undergone severe depletion of their NK precursor and/or NK cells resulting in a state of immune deficiency.

The cells of the NK precursor, NK and/or KIL cell lines in a cellular composition, in particular an expanded cellular composition provided for by a method of the invention, may be transfected with a desired gene that can be used for treatment of genetic diseases. Genetic diseases may also be treated by introducing a gene that may compliment the deficiency or the abnormality of the gene causing the diseases into NK precursor, NK and/or KIL cells and then introducing the cells into a subject. For example, a normal wild type gene that when mutated may cause a disease such as β-thalassemia (Mediterranean anemia), sickle cell anemia, ADA deficiency, recombinase deficiency, recombinase regulatory gene deficiency and the like, may be transferred into the cells of the NK precursor, NK and/or KIL cell lines, e.g., by homologous or random recombination, and the cells can be introduced into a patient.

Yet another application of the invention permits the use of a drug in a concentration higher than may be allowed otherwise, e.g., at a level which is normally considered to be dangerous, by providing drug resistance to the NK precursor, NK and/or KIL cells. In particular, it is possible to carry out the treatment using an anticancer drug in high concentration by transferring a gene having drug resistance against the anticancer drug, e.g., a multiple drug resistant gene, into cells of the NK precursor, NK and/or KIL cell lines in a cellular composition of the invention.

As discussed herein, RNAi may be used in conjunction with the invention, either as a research tool or as a therapeutic (see, for example, U.S. Pat. Pub. No. 2003/0084471 A1; International Patent Appl. Nos. PCT/US04/41714, and PCT/US04/037475).

It is also possible to genetically engineer and insert a gene encoding a ribozyme, an antisense nucleic acid or the like (e.g., siRNA) or another suitable gene into cells of the NK precursor, NK and/or KIL cell lines to control expression of a specific gene product in the cells or to inhibit susceptibility to diseases. For example, the cells of the NK precursor, NK and/or KIL cell lines can be subjected to gene modification to express an antisense nucleic acid, siRNA, or a ribozyme, which can prevent growth of hematic pathogens such as HIV, HTLV-I, HTLV-II and the like in cells of the NK precursor, NK and/or KIL cell lines.

In a further embodiment, cells of the NK precursor, NK and/or KIL cell lines of a cellular composition of the invention are created which express known inhibitory genes of HIV replication, such as RNA decoys or the Tat- or Rev-responsive elements, or a dominant negative mutant of the Rev transactivator protein. Cells of the NK precursor, NK and/or KIL cell lines derived from hematopoietic progenitor cells carrying these genes would provide a potentially limitless and defined source of HIV-resistant lymphocyte progenitors.

The cellular compositions comprising cells of the NK precursor, NK and/or KIL cell lines can be introduced into a vertebrate, which is a recipient of cell grafting, by, for example, conventional intravenous administration.

NK cell lymphoma/leukemia is a group of recently characterized hematolymphoid malignancies that may be treated using NK precursor, NK and/or KIL cells; and/or NK precursor, NK and/or KIL cell line progenitor cells of the invention, either by targeting appropriate cells in vivo to express Jagged2, or functional fragments thereof, or by ex vivo treatment.

In a further embodiment, NK precursor, NK and/or KIL cells produced by the present invention may be used to treat cancer. NK precursor, NK and/or KIL cells, which are produced by the present invention, are functionally characterized by their ability to kill certain tumor cells without prior sensitization and to produce pro-inflammatory cytokines, especially interferon gamma (IFNγ), following activation.

In a further embodiment, NK precursor, NK and/or KIL cells produced by the present invention may be used in combination with an antibody, antibody fragment, and/or antibody derivative (e.g., one or more antibody having specificity to one or more antigens of a cancer or infected cell) to treat cancer or infection. For example, antibody-dependent cell-mediated cytotoxicity using NK or KIL cells, which may be expanded in vitro, in combination with an antibody (e.g., Rituximab, a monoclonal Ab against CD20, which is expressed by many non-Hodgkin's lymphomas) may be used to produce an improved. Examples of additional antibodies that may be used with the invention include, but is not limited to, alemtuzumab and tositumomab, which are typically used to treat leukaemia (typically, B-cell chronic lymphocytic leukaemia), gemtuzumab, which is in clinical trials for the treatment of acute myeloid leukaemia, trastuzumab, which is typically used to treat breast cancer, cetuximab, oncolym, LL2, natalizumab, 3F8, bevacizumab, ranibizumab, omalizumab, pertuzumab, visilizumab, daclizumab, volociximab, and/or fontolizumab.

Those skilled in the field of molecular biology will understand that any of a wide variety of expression systems may be used to provide a recombinant protein or protein fragment. The methods of transformation, transfection or transduction, and the choice of expression vehicle (vector), will depend on the host system, desired stability and/or availability of appropriate restriction endonuclease sites. Transformation and transfection methods are described, e.g., in Ausubel, et al., 1997, expression vehicles may be chosen from those provided, for example, in Pouwels et al., 1985, Supp. 1987, or known in the art.

Techniques and software for determining sequence homology or identity between two or more amino acid or nucleic acid sequences are well known in the art. Notch receptors and their ligands and homologues/orthologues/paralogues thereof can be identified by techniques known in the art, for example, by probing genomic or cDNA libraries with Jagged2 derived probes under conditions of medium to high stringency. Homologues/orthologues/paralogues can also be identified using PCR, for example, using targeted degenerate primers to amplify nucleic acid sequences which may encode for the corresponding conserved amino acid sequences. In addition, homologues/orthologues/paralogues may be identified by sequence alignment using sequence databases, e.g., expressed sequence tag (EST) databases.

Constructs of the invention used to express human Jagged2, mouse Jagged2, rat Jagged2 and homologues, orthologues and/or paralogues of Jagged2 may be prepared for introduction into a HSC and may comprise a replication system recognized by the host, and will preferably also include transcriptional and translational regulatory sequences operably linked to the nucleotide sequence encoding Jagged2. The vector may be an autonomously replicating vector, a viral or phage vector, a transposable element, an integrating vector or an extrachromosomal element, such as a minichromosome or an artificial chromosome. Such vectors may be prepared by means of standard recombinant techniques well known in the art. See for example, Ausubel et al., 1992, Sambrook et al., 2001, and U.S. Pat. No. 5,837,492.

The proteins of the invention (e.g., Jagged2) may be cotranslationally, post-translationally or spontaneously modified, for example, by acetylation, farnesylation, glycosylation, myristoylation, methylation, prenylation, phosphorylation, palmitoylation, sulfation, ubiquitination and the like (Wold, 1981).

Subjects contemplated by the invention include, but are not limited to, animals, such as an animal disease model, and mammals, such as domestic livestock and humans.

Peptides produced in a cell of the invention and/or a cell of the invention may be formulated as a pharmaceutically acceptable compound or composition. Excipients, diluents and/or carriers are known in the art, for example, see Remington's Pharmaceutical Sciences, $18^{th}$ ed., and Goodman and Gilman's, The Pharmacological Basis of Therapeutics, $10^{th}$ ed., 2001.

The present invention, in one embodiment, demonstrates that Jagged2, a Notch receptor ligand, stimulates the development of NK precursor and/or NK cells from post-5-fluorouracil bone marrow MNC and Lin$^-$ Sca-1$^+$ c-kit$^+$ HSCs in the presence of the OP-9S stromal fibroblast cells, Flt3L and IL-7. A culture system of the invention supports NK cell development for 2-3 months, increasing the ability to establish continuous NK cell lines. An example of such cell lines is designated as KIL. KIL depends on IL-7 for survival and proliferation and is NK1.1$^+$, CD3$^-$, TCRαβ$^-$, TCRδγ$^-$, CD4$^-$, CD8$^-$, CD19$^-$, CD25$^+$, CD43$^+$, CD45$^+$, CD49b$^-$, CD51$^+$, CD94$^+$, NKG2D$^+$, Mac-1$^{-/low}$, B220$^-$, c-kit$^+$, perforin I$^+$, granzyme B$^+$, Notch-1$^+$, and cytotoxic. Like normal NK cells, the T-cell receptor-β loci of KIL remain in the germ-line configuration.

In response to IL-2, KIL proliferates extensively (increasing cell number by ≈$10^{10}$ fold) and terminally differentiates into adherent, hypergranular NK cells. The KIL cell line preserves most properties of the normal NK precursors and NK cell lines. As such, KIL provides a valuable medical asset and will greatly extend further NK cell research.

All references, including publications, patents, and patent applications, cited herein are hereby incorporated by reference to the same extent as if each reference were individually and specifically indicated to be incorporated by reference and were set forth in its entirety herein.

REFERENCES

Artavanis-Tsakonas et al., Science, 284 (1999) 770.
Ausubel et al., *Short Protocols in Molecular Biology*, $2^{nd}$ ed. (1992) Greene Publishing Associates, NY.
Ausubel et al., *Current Protocols in Molecular Biology* (1997) John Wiley & Sons, NY.
Bettenhausen et al., Development, 121 (1995) 2407.
Bradley et al., Current Topics in Devel. Biol., 20 (1986) 357.
Bradshaw et. al., *Handbook of Cell Signaling* (2003) Academic Press, San Diego, Calif.
Carlyle et al., J. Exp. Med., 186 (1997) 173.
del Amo et al., Genomics, 15 (1993) 259.
Dunwoodie et al., Development, 124 (1997) 3065.
Felli et al., Int. Immunol., 11 (1999) 1017.
Fibashir et al., Genes Dev., 15 (2001) 188.
Freshney, *Animal Cell Culture: A Manual of Basic Techniques*, $3^{rd}$ ed. (1994) John Wiley & Sons, NY.
Gait, *Oligonucleotide synthesis: A Practical Approach* (1984) Oxford University Press, NY.
Goodman et al., *The Pharmacological Basis of Therapeutics*, $10^{th}$ ed. (2001) McGraw-Hill, NY.
Glover, *DNA Cloning: A Practical Approach, Volumes I and II* (1985) IRL Press Ltd., Oxford.
Guilbault et al., *Immobilized Cells and Enzymes: A Practical Approach* (1984) IRL Press Ltd., Oxford.
Hames et al., *Transcription and Translation: A Practical Approach* (1984) IRL Press Ltd., Oxford.
Hames et al., *Nucleic Acid Hybridization: A Practical Approach* (1985) IRL Press Ltd., Oxford.
Hill et al., Methods in Enzymology, 225 (1993) 664.
Hogan et al., *Manipulating the Mouse Embryo: A Laboratory Manual* (1986) Cold Spring Harbor Laboratory Press, Cold Spring Harbor, N.Y.
Hozumi et al., Nat. Immunol., 5 (2004) 638.
Hutvagner et al., Curr. Opin. Genet. Dev., 12 (2002) 225.
Ikawa et al., J. Exp. Med., 190 (1999) 1617.
Jaleco et al., J. Exp. Med., 194 (2001) 991.
Jiang et al., Genes Dev., 12 (1998) 1046.
Karlhofer et al., J. Exp. Med., 181 (1995) 1785.
Katsura., Nat. Rev. Immunol., 2 (2002) 127.
Kim et al., Nat. Immunol., 3 (2002) 523.
King et al., Proc. Nat. Acad. Sci. U.S.A., 99 (2002) 4508.
Kodama et al., Exp. Hematol., 22 (1994) 979.
Kondo et al., Cell, 91 (1997) 661.
Konstantinidis et al., Exp. Hemat. 33 (2005) 159.
Kubota et al., J. Immunol., 163 (1999) 212.
Lardelli et al., Mech. Dev., 46 (1994) 123.
Lewis et al., Semin. Cell Dev. Biol., 9 (1998) 583.
Lindsell et al., Cell, 80 (1995) 909.
Luo et al., Mol. Cell Biol., 17 (1997) 6057.
Nakano et al., Science, 265 (1994) 1098
Perbal, et al., *A Practical Guide to Molecular Cloning* (1988) John Wiley & Sons, NY.
Pouwels et al., *Cloning Vectors: A Laboratory Manual* (1985, Supp. 1987) Elsevier Scientific Publishing, Amsterdam.
Pui et al., Immunity, 11 (1999) 299.
*Remington's Pharmaceutical Sciences*, $18^{th}$ ed. (1990) Mack Publishing Co., Easton, Pa.
Radtke et al., Immunity, 10 (1999) 547.
Radtke et al., Nat. Immunol., 5 (2004) 247.
Robey et al., Curr. Opin. Genet. Dev., 7 (1997) 551.
Robertson, et. al., *Teratocarcinomas and Embryonic Stem Cells: A Practical Approach* (1987) IRL Press, Washington, D.C.
Sambrook et al., *Molecular Cloning*, $2^{nd}$ ed. (1989) Cold Spring Harbor Laboratory Press, NY.
Shawber et al., Dev. Biol., 180 (1996) 370.
Schmitt et al., Immunity, 17 (2002) 749.
Schmitt et al., Nat. Immunol., 5 (2004) 410.
Schmitt et al., J. Exp. Med., 200 (2004) 469.
Shuey et al., Drug Discovery Today, 7 (2002) 1040.
Shutter et al., Genes Dev., 14 (2000) 1313.
Simpson et al., Nature, 375 (1995) 736.
Spangrude et al., Blood, 85 (1995) 1006.
Spits et al., Immunol Rev. 165 (1998) 75.
Tanigaki et al., Nat. Immunol., 3 (2002) 443.
Tax et al., Nature, 368 (1994) 150.
Tsai et al., Genes Dev., 8 (1994) 2831.
Tsai et al., Blood, 96 (2000) 950.
Tsai et al., Proc. Nat. Acad. Sci. U.S.A., 90 (1993) 7153.
Uyttendaele et al., Development, 122 (1996) 2251.
Weinmaster et al., Development, 116 (1992) 931.
Wold, Annu. Rev. Biochem., 50 (1981) 783.
Yokoyama et al., Annu. Rev. Immunol., 22 (2004) 405.
Zamore, et al., Cell, 101 (2000) 25.

What is claimed is:

1. A method for producing natural killer precursor and/or natural killer cells in vitro or ex vivo, the method comprising bringing a population of hematopoietic progenitor cells or light-density mononuclear cells or embryonic stem cells into contact with IL-7, Flt3L and Jagged2, and culturing said population of hematopoietic progenitor or light-density mononuclear cells or embryonic stem cells for between 35 and 45 days, whereby a natural killer precursor and/or natural killer cell is produced.

2. The method according to claim 1, wherein said Jagged2 is provided by a population of cells expressing Jagged2.

3. The method according to claim 2, wherein said population of cells is OP-9 stromal cells as deposited with ATCC, deposit number PTA-10785, and which have been subsequently engineered to express Jagged2.

4. The method according to claim 1, wherein the light-density mononuclear cells, hematopoietic progenitor cells or embryonic stem cells are obtained from bone marrow.

5. The method according to claim 4, further comprising selecting $Lin^-$ $Sca-1^+$ $c-Kit^+$ light-density mononuclear cells, hematopoietic progenitor cells or embryonic stem cells.

6. The method according to claim 1, wherein the natural killer precursor cells are $NK1.1^+$, $CD3^-$, $TCR\alpha\beta^-$, $TCR\delta\gamma^-$, $CD4^-$, $CD8^-$, $CD19^-$, $CD25^+$, $CD43^+$, $CD45^+$, $CD49b^-$, $CD51^+$, $CD94^+$, $NKG2D^+$, $Mac-1^{-/low}$, $B220^-$, $c-kit^+$, perforin $I^+$, granzyme $B^+$, $Notch-1^+$, and cytotoxic.

7. The method according to claim 1, wherein Jagged2 is human Jagged2.

8. The method according to claim 1, further comprising obtaining said light-density mononuclear cells, hematopoietic progenitor cells or embryonic stem cell from a human subject.

9. The method according to claim 2, wherein said population of stromal cells expressing Jagged2 comprises a population of stromal cells having a retroviral vector sequence encoding said Jagged2.

10. A method for preparing a natural killer precursor cell or natural killer cell useful for the treatment of cancer or viral infection, comprising:

bringing a population of light-density mononuclear cells, hematopoietic progenitor cells or embryonic stem cells into contact with IL-7, Flt3L and a population of cells expressing Jagged2 in vitro or ex vivo;

co-culturing said light-density mononuclear cells or hematopoietic progenitor cells or embryonic stem cells and said cells expressing Jagged2 to produce a population of cells enriched for natural killer precursor cell or natural killer cell;

isolating said natural killer precursor cell or natural killer cell; and admixing said natural killer precursor cell or natural killer cell and a pharmaceutically acceptable vehicle.

11. The method according to claim 10, wherein said population of light-density mononuclear cells, hematopoietic progenitor cells or embryonic stem cells from bone marrow are obtained from a sample taken from a subject.

12. The method according to claim 11, further comprising selecting a Lin– Sca-1$^+$ c-Kit$^+$ hematopoietic progenitor cell or embryonic stem cell.

13. The method according to claim 12, further comprising passaging said co-culture in media containing Flt3L, IL-7, and stem cell factor for a period of about 3 months.

14. The method according to claim 10, wherein said population of cells expressing Jagged2 is a stromal cell.

15. The method according to claim 14, wherein said population of cells is OP-9 stromal cells as deposited with ATCC, deposit number PTA 10785, that has been subsequently engineered to express Jagged2.

16. The method according to claim 10, wherein Jagged2 is human Jagged2.

17. The method according to claim 10, wherein said cell expressing Jagged2 comprises a retroviral vector sequence encoding said Jagged2.

18. The method according to claim 10, wherein the natural kill precursor cell or natural killer cell is NK1.1$^+$, CD3$^-$, TCRαβ$^-$, TCRδγ$^-$, CD4$^-$, CD8$^-$, CD19$^-$, CD25$^+$, CD43$^+$, CD45$^+$, CD49b$^-$, CD51$^+$, CD94$^+$, NKG2D$^+$, Mac-1$^{-/low}$, B220$^-$, c-kit$^+$, perforin I$^+$, granzyme B$^+$, Notch-1$^+$, and cytotoxic.

19. The method according to claim 10, further comprising producing an immortalized natural killer cell line.

20. The method according to claim 18, further comprising producing an immortalized natural killer cell line.

21. The method according to claim 1, wherein about 100 to about 160 times the amount of natural killer precursor cells or natural killer cells are produced, relative to the amount of natural killer precursor cells or natural killer cells produced in the absence of Jagged2.

* * * * *